US006426332B1

(12) United States Patent
Rueger et al.

(10) Patent No.: US 6,426,332 B1
(45) Date of Patent: *Jul. 30, 2002

(54) MATRIX-FREE OSTEOGENIC DEVICES, IMPLANTS AND METHODS OF USE THEREOF

(75) Inventors: David C. Rueger, Southborough; Marjorie M. Tucker, Holliston, both of MA (US)

(73) Assignee: Stryker Corporation, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/887,901

(22) Filed: Jun. 22, 2001

Related U.S. Application Data

(63) Continuation of application No. 09/019,339, filed on Feb. 5, 1998, now Pat. No. 6,281,195.

(60) Provisional application No. 60/037,327, filed on Feb. 7, 1997, and provisional application No. 60/047,909, filed on May 29, 1997.

(51) Int. Cl.[7] .......................... A61K 9/00; A61K 38/02; A61K 38/18

(52) U.S. Cl. .......................... 514/21; 424/423; 514/12; 604/506; 604/522

(58) Field of Search ................................ 424/422, 423, 424/426; 514/8, 12, 21; 604/500, 506, 518, 522

(56) References Cited

U.S. PATENT DOCUMENTS

| | | | | | |
|---|---|---|---|---|---|
| 5,158,934 | A | * | 10/1992 | Ammann et al. | 514/12 |
| 5,290,271 | A | * | 3/1994 | Jernberg | 604/891.1 |
| 5,385,887 | A | * | 1/1995 | Yin et al. | 514/12 |
| 5,531,791 | A | * | 7/1996 | Wolfinbarger, Jr. | 623/16 |
| 5,674,844 | A | * | 10/1997 | Kuberasampath et al. | 514/12 |
| 5,693,615 | A | * | 12/1997 | Stone | 514/12 |
| 6,187,742 | B1 | * | 2/2001 | Wozney et al. | 514/2 |
| 6,281,195 | B1 | * | 8/2001 | Rueger et al. | 514/21 |

FOREIGN PATENT DOCUMENTS

| | | | |
|---|---|---|---|
| EP | 0 308 238 | * | 3/1989 |
| EP | 0 321 277 | * | 6/1989 |
| EP | 0 419 275 | * | 3/1991 |
| EP | 0 688 869 | * | 12/1995 |
| FR | 2564732 | * | 11/1985 |
| WO | WO-86/00526 | * | 1/1986 |
| WO | WO-93/25246 | * | 12/1993 |
| WO | WO-95/33502 | * | 12/1995 |
| WO | WO-96/40297 | * | 12/1996 |
| WO | WO-97/21447 | * | 6/1997 |

* cited by examiner

*Primary Examiner*—Jeffrey E. Russel
(74) *Attorney, Agent, or Firm*—Fish & Neave; James F. Haley, Jr.; Karen Mangasarian

(57) ABSTRACT

Provided herein are methods for inducing bone formation in a mammal sufficient to fill a defect defining a void, wherein osteogenic protein is provided alone or dispersed in a biocompatible non-rigid, amorphous carrier having no defined surfaces. The methods and devices provide injectable formulations for filling critical size defects, as well as for accelerating the rate and enhancing the quality of bone formation in non-critical size defects.

9 Claims, No Drawings

```
                    SEQUENCE LISTING


(1) GENERAL INFORMATION:

   (iii) NUMBER OF SEQUENCES: 8


(2) INFORMATION FOR SEQ ID NO: 1:

     (i) SEQUENCE CHARACTERISTICS:
          (A) LENGTH: 1822 base pairs
          (B) TYPE: nucleic acid
          (C) STRANDEDNESS: single
          (D) TOPOLOGY: linear

    (ii) MOLECULE TYPE: cDNA

   (iii) HYPOTHETICAL: No

    (iv) ANTI-SENSE: No

    (vi) ORIGINAL SOURCE:
          (A) ORGANISM: HOMO SAPIENS
          (F) TISSUE TYPE: HIPPOCAMPUS

    (ix) FEATURE:
          (A) NAME/KEY: CDS
          (B) LOCATION: 49..1341
          (C) IDENTIFICATION METHOD: experimental
          (D) OTHER INFORMATION: /function= "OSTEOGENIC PROTEIN"
               /product= "OP1"
```

-continued

```
              /evidence= EXPERIMENTAL
              /standard_name= "OP1"

    (xi) SEQUENCE DESCRIPTION: SEQ ID NO: 1:

GGTGCGGGCC CGGAGCCCGG AGCCCGGGTA GCGCGTAGAG CCGGCGCG ATG CAC GTG      57
                                                     Met His Val
                                                       1

CGC TCA CTG CGA GCT GCG GCG CCG CAC AGC TTC GTG GCG CTC TGG GCA     105
Arg Ser Leu Arg Ala Ala Ala Pro His Ser Phe Val Ala Leu Trp Ala
      5                  10                  15

CCC CTG TTC CTG CTG CGC TCC GCC CTG GCC GAC TTC AGC CTG GAC AAC     153
Pro Leu Phe Leu Leu Arg Ser Ala Leu Ala Asp Phe Ser Leu Asp Asn
 20                  25                  30                  35

GAG GTG CAC TCG AGC TTC ATC CAC CGG CGC CTC CGC AGC CAG GAG CGG     201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC     249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG     297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC     345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC     393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC     441
Pro Pro Leu Ala Ser Leu Gln Asp Ser His Phe Leu Thr Asp Ala Asp
                120                 125                 130

ATG GTC ATG AGC TTC GTC AAC CTC GTG GAA CAT GAC AAG GAA TTC TTC     489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC     537
His Pro Arg Tyr His His Arg Glu Phe Arg Phe Asp Leu Ser Lys Ile
        150                 155                 160

CCA GAA GGG GAA GCT GTC ACG GCA GCC GAA TTC CGG ATC TAC AAG GAC     585
Pro Glu Gly Glu Ala Val Thr Ala Ala Glu Phe Arg Ile Tyr Lys Asp
    165                 170                 175

TAC ATC CGG GAA CGC TTC GAC AAT GAG ACG TTC CGG ATC AGC GTT TAT     633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC     681
Gln Val Leu Gln Glu His Leu Gly Arg Glu Ser Asp Leu Phe Leu Leu
                200                 205                 210

GAC AGC CGT ACC CTC TGG GCC TCG GAG GAG GGC TGG CTG GTG TTT GAC     729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG     777
Ile Thr Ala Thr Ser Asn His Trp Val Val Asn Pro Arg His Asn Leu
        230                 235                 240

GGC CTG CAG CTC TCG GTG GAG ACG CTG GAT GGG CAG AGC ATC AAC CCC     825
Gly Leu Gln Leu Ser Val Glu Thr Leu Asp Gly Gln Ser Ile Asn Pro
    245                 250                 255

AAG TTG GCG GGC CTG ATT GGG CGG CAC GGG CCC CAG AAC AAG CAG CCC     873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC     921
Phe Met Val Ala Phe Phe Lys Ala Thr Glu Val His Phe Arg Ser Ile
```

-continued

```
                280                 285                 290

CGG TCC ACG GGG AGC AAA CAG CGC AGC CAG AAC CGC TCC AAG ACG CCC      969
Arg Ser Thr Gly Ser Lys Gln Arg Ser Gln Asn Arg Ser Lys Thr Pro
            295                 300                 305

AAG AAC CAG GAA GCC CTG CGG ATG GCC AAC GTG GCA GAG AAC AGC AGC     1017
Lys Asn Gln Glu Ala Leu Arg Met Ala Asn Val Ala Glu Asn Ser Ser
        310                 315                 320

AGC GAC CAG AGG CAG GCC TGT AAG AAG CAC GAG CTG TAT GTC AGC TTC     1065
Ser Asp Gln Arg Gln Ala Cys Lys Lys His Glu Leu Tyr Val Ser Phe
    325                 330                 335

CGA GAC CTG GGC TGG CAG GAC TGG ATC ATC GCG CCT GAA GGC TAC GCC     1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG     1161
Ala Tyr Tyr Cys Glu Gly Glu Cys Ala Phe Pro Leu Asn Ser Tyr Met
                360                 365                 370

AAC GCC ACC AAC CAC GCC ATC GTG CAG ACG CTG GTC CAC TTC ATC AAC     1209
Asn Ala Thr Asn His Ala Ile Val Gln Thr Leu Val His Phe Ile Asn
            375                 380                 385

CCG GAA ACG GTG CCC AAG CCC TGC TGT GCG CCC ACG CAG CTC AAT GCC     1257
Pro Glu Thr Val Pro Lys Pro Cys Cys Ala Pro Thr Gln Leu Asn Ala
        390                 395                 400

ATC TCC GTC CTC TAC TTC GAT GAC AGC TCC AAC GTC ATC CTG AAG AAA     1305
Ile Ser Val Leu Tyr Phe Asp Asp Ser Ser Asn Val Ile Leu Lys Lys
    405                 410                 415

TAC AGA AAC ATG GTG GTC CGG GCC TGT GGC TGC CAC TAGCTCCTCC          1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG   1411

GAACCAGCAG ACCAACTGCC TTTTGTGAGA CCTTCCCCTC CCTATCCCCA ACTTTAAAGG   1471

TGTGAGAGTA TTAGGAAACA TGAGCAGCAT ATGGCTTTTG ATCAGTTTTT CAGTGGCAGC   1531

ATCCAATGAA CAAGATCCTA CAAGCTGTGC AGGCAAAACC TAGCAGGAAA AAAAAACAAC   1591

GCATAAAGAA AAATGGCCGG GCCAGGTCAT TGGCTGGGAA GTCTCAGCCA TGCACGGACT   1651

CGTTTCCAGA GGTAATTATG AGCGCCTACC AGCCAGGCCA CCCAGCCGTG GGAGGAAGGG   1711

GGCGTGGCAA GGGGTGGGCA CATTGGTGTC TGTGCGAAAG GAAAATTGAC CCGGAAGTTC   1771

CTGTAATAAA TGTCACAATA AAACGAATGA ATGAAAAAAA AAAAAAAAAA A            1822


(2) INFORMATION FOR SEQ ID NO: 2:

     (i) SEQUENCE CHARACTERISTICS:
          (A) LENGTH: 431 amino acids
          (B) TYPE: amino acid
          (D) TOPOLOGY: linear

    (ii) MOLECULE TYPE: protein

    (xi) SEQUENCE DESCRIPTION: SEQ ID NO: 2:

Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
             20                  25                  30

Leu Asp Asn Glu Val His Ser Ser Phe Ile His Arg Arg Leu Arg Ser
         35                  40                  45

Gln Glu Arg Arg Glu Met Gln Arg Glu Ile Leu Ser Ile Leu Gly Leu
     50                  55                  60

Pro His Arg Pro Arg Pro His Leu Gln Gly Lys His Asn Ser Ala Pro
```

-continued

```
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```

(2) INFORMATION FOR SEQ ID NO: 3:

(i) SEQUENCE CHARACTERISTICS:
(A) LENGTH: 102 amino acids
(B) TYPE: amino acid
(D) TOPOLOGY: linear (ii) MOLECULE TYPE: protein (ix) FEATURE:

-continued (A) NAME/KEY: Protein
(B) LOCATION: 1..102
(D) OTHER INFORMATION: /label= OPX
/note= "Wherein each Xaa is independently selected from a group of one or more specified amino acids as defined in the specification"

(xi) SEQUENCE DESCRIPTION: SEQ ID NO: 3:

```
Cys Xaa Xaa His Glu Leu Tyr Val Xaa Phe Xaa Asp Leu Gly Trp Xaa
 1               5                  10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100
```

(2) INFORMATION FOR SEQ ID NO: 4:

(i) SEQUENCE CHARACTERISTICS:
(A) LENGTH: 97 amino acids
(B) TYPE: amino acid
(D) TOPOLOGY: linear (ii) MOLECULE TYPE: protein (ix) FEATURE:
(A) NAME/KEY: Protein
(B) LOCATION: 1..97
(D) OTHER INFORMATION: /label= Generic Sequence 7
/note= "Wherein each Xaa is independently selected from a group of one or more specified amino acids as defined in the specification"

(xi) SEQUENCE DESCRIPTION: SEQ ID NO: 4:

```
Leu Xaa Xaa Xaa Phe Xaa Xaa Xaa Gly Trp Xaa Xaa Xaa Xaa Xaa Xaa
  1               5                  10                  15

Pro Xaa Xaa Xaa Xaa Ala Xaa Tyr Cys Xaa Gly Xaa Cys Xaa Xaa Pro
            20                  25                  30

Xaa Xaa Xaa Xaa Xaa Xaa Xaa Xaa Asn His Ala Xaa Xaa Xaa Xaa Xaa
        35                  40                  45

Xaa Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
                85                  90                  95

Xaa
```

(2) INFORMATION FOR SEQ ID NO: 5:

(i) SEQUENCE CHARACTERISTICS:
(A) LENGTH: 102 amino acids
(B) TYPE: amino acid
(D) TOPOLOGY: linear (ii) MOLECULE TYPE: protein -continued (ix) FEATURE:
(A) NAME/KEY: Protein
(B) LOCATION: 1..102
(D) OTHER INFORMATION: /label= Generic Sequence 8
/note= "Wherein each Xaa is independently selected from a group of one or more specified amino acids as defined in the specification"

(xi) SEQUENCE DESCRIPTION: SEQ ID NO: 5:

```
Cys Xaa Xaa Xaa Xaa Leu Xaa Xaa Xaa Phe Xaa Xaa Xaa Gly Trp Xaa
  1               5                  10                  15

Xaa Xaa Xaa Xaa Xaa Pro Xaa Xaa Xaa Xaa Ala Xaa Tyr Cys Xaa Gly
             20                  25                  30

Xaa Cys Xaa Xaa Pro Xaa Xaa Xaa Xaa Xaa Xaa Xaa Xaa Asn His Ala
         35                  40                  45

Xaa Xaa Xaa Xaa Xaa Xaa Xaa Xaa Xaa Xaa Xaa Xaa Xaa Xaa Xaa Xaa
     50                  55                  60

Xaa Cys Cys Xaa Pro Xaa Xaa Xaa Xaa Xaa Xaa Xaa Xaa Leu Xaa Xaa
 65                  70                  75                  80

Xaa Xaa Xaa Xaa Xaa Val Xaa Leu Xaa Xaa Xaa Xaa Xaa Met Xaa Val
                 85                  90                  95

Xaa Xaa Cys Xaa Cys Xaa
            100
```

(2) INFORMATION FOR SEQ ID NO: 6:

(i) SEQUENCE CHARACTERISTICS:
(A) LENGTH: 5 amino acids
(B) TYPE: amino acid
(D) TOPOLOGY: linear (ii) MOLECULE TYPE: protein (ix) FEATURE:
(A) NAME/KEY: Protein
(B) LOCATION: 1..5
(D) OTHER INFORMATION: /label= Consensus Sequence
/note= "Wherein each Xaa is independently selected from a group of one or more specified amino acids as defined in the specification"

(xi) SEQUENCE DESCRIPTION: SEQ ID NO: 6:

```
Cys Xaa Xaa Xaa Xaa
  1               5
```

(2) INFORMATION FOR SEQ ID NO: 7:

(i) SEQUENCE CHARACTERISTICS:
(A) LENGTH: 97 amino acids
(B) TYPE: amino acid
(D) TOPOLOGY: linear (ii) MOLECULE TYPE: protein (ix) FEATURE:
(A) NAME/KEY: Protein
(B) LOCATION: 1..97
(D) OTHER INFORMATION: /label= Generic Sequence 10
/note= "Wherein each Xaa is independently selected from a group of one or more specified amino acids as defined in the specification"

(xi) SEQUENCE DESCRIPTION: SEQ ID NO: 7:

```
Xaa Xaa Xaa Xaa Xaa Xaa Xaa Xaa Xaa Xaa Xaa Xaa Xaa Xaa Xaa Xaa
  1               5                  10                  15

Pro Xaa Xaa Xaa Xaa Xaa Xaa Xaa Cys Xaa Gly Xaa Cys Xaa Xaa Xaa
```

-continued

```
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Cys Xaa Pro
    50                  55                  60

Xaa Xaa Xaa Xaa Xaa Xaa Xaa Xaa Leu Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Cys Xaa Cys
                85                  90                  95

Xaa

(2) INFORMATION FOR SEQ ID NO: 8:

     (i) SEQUENCE CHARACTERISTICS:
          (A) LENGTH: 102 amino acids
          (B) TYPE: amino acid
          (D) TOPOLOGY: linear

    (ii) MOLECULE TYPE: protein

    (ix) FEATURE:
          (A) NAME/KEY: Protein
          (B) LOCATION: 1..102
          (D) OTHER INFORMATION: /label= Generic Sequence 9
               /note= "Wherein each Xaa is independently selected from a
               group of one or more specified amino acids as
               defined in the specification"

    (xi) SEQUENCE DESCRIPTION: SEQ ID NO: 8:

Cys Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Pro Xaa Xaa Xaa Xaa Xaa Xaa Xaa Cys Xaa Gly
            20                  25                  30

Xaa Cys Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Cys Xaa Pro Xaa Xaa Xaa Xaa Xaa Xaa Xaa Xaa Leu Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Cys Xaa Cys Xaa
            100
```

MATRIX-FREE OSTEOGENIC DEVICES, IMPLANTS AND METHODS OF USE THEREOF

This application is a continuation of U.S. application Ser. No. 09/019,339, filed Feb. 5, 1998, now U.S. Pat. No. 6,281,185, the entire disclosure of which is incorporated by reference herein, which claims the benefit of prior U.S. application Ser. Nos. 60/037,327, filed Feb. 7, 1997 and 60/047,909, filed May 29, 1997, the entire disclosures of both of which are incorporated by reference herein.

FIELD OF THE INVENTION

The invention disclosed herein relates to materials and methods for repairing bone defects using osteogenic proteins.

BACKGROUND OF THE INVENTION

A class of proteins now have been identified that are competent to act as true chondrogenic tissue morphogens, able, on their own, to induce the proliferation and differentiation of progenitor cells into functional bone, cartilage, tendon, and/or ligamentous tissue. These proteins, referred to herein as "osteogenic proteins" or "morphogenic proteins" or "morphogens," includes members of the family of bone morphogenetic proteins (BMPs) which were initially identified by their ability to induce ectopic, endochondral bone morphogenesis. The osteogenic proteins generally are classified in the art as a subgroup of the TGF-β superfamily of growth factors (Hogan (1996) *Genes& Development* 10:1580–1594). Members of the morphogen family of proteins include the mammalian osteogenic protein-1 (OP-1, also known as BMP-7, and the Drosophila homolog 60A), osteogenic protein-2 (OP-2, also known as BMP-8), osteogenic protein-3 (OP-3), BMP-2 (also known as BMP-2A or CBMP-2A, and the Drosophila homolog DPP), BMP-3, BMP-4 (also known as BMP-2B or CBMP-2B), BMP-5, BMP-6 and its murine homolog Vgr-1, BMP-9, BMP-10, BMP-11, BMP-12, GDF3 (also known as Vgr2), GDF8, GDF9, GDF10, GDF11, GDF12, BMP-13, BMP-14, BMP-15, GDF-5 (also known as CDMP-1 or MP52), GDF-6 (also known as CDMP-2), GDF-7 (also known as CDMP-3), the Xenopus homolog Vg1 and NODAL, UNIVIN, SCREW, ADMP, and NEURAL. Members of this family encode secreted polypeptide chains sharing common structural features, including processing from a precursor "pro-form" to yield a mature polypeptide chain competent to dimerize, and containing a carboxy terminal active domain of approximately 97–106 amino acids. All members share a conserved pattern of cysteines in this domain and the active form of these proteins can be either a disulfide-bonded homodimer of a single family member, or a heterodimer of two different members (see, e.g., Massague (1990) *Annu. Rev. Cell Biol.* 6:597; Sampath, et al. (1990) *J. Biol. Chem.* 265:13198). See also, U.S. Pat. No. 5,011,691; U.S. Pat. No. 5,266,683, Ozkaynak et al. (1990) *EMBO J.* 9: 2085–2093, Wharton et al. (1991) *PNAS* 88:9214–9218), (Ozkaynak (1992) *J. Biol. Chem.* 267:25220–25227 and U.S. Pat. No. 5,266,683); (Celeste et al. (1991) *PNAS* 87:9843–9847); (Lyons et al. (1989 ) *PNAS* 86:4554–4558). These disclosures describe the amino acid and DNA sequences, as well as the chemical and physical characteristics of these osteogenic proteins. See also Wozney et al. (1988) *Science* 242:1528–1534); BMP 9 (WO93/00432, published Jan. 7, 1993); DPP (Padgett et al. (1987) *Nature* 325:81–84; and Vg-1 (Weeks (1987) *Cell* 51:861–867).

Thus, true osteogenic proteins capable of inducing the above-described cascade of morphogenic events that result in endochondral bone formation have now been identified, isolated, and cloned. Whether naturally-occurring or synthetically prepared, these osteogenic factors, when implanted in a mammal in association with a conventional matrix or substrate that allows the attachment, proliferation and differentiation of migratory progenitor cells, have been shown to induce recruitment of accessible progenitor cells and stimulate their proliferation, thereby inducing differentiation into chondrocytes and osteoblasts, and further inducing differentiation of intermediate cartilage, vascularization, bone formation, remodeling, and finally marrow differentiation. Furthermore, numerous practitioners have demonstrated the ability of these osteogenic proteins, when admixed with either naturally-sourced matrix materials such as collagen or synthetically-prepared polymeric matrix materials, to induce bone formation, including endochondral bone formation under conditions where true replacement bone otherwise would not occur. For example, when combined with a matrix material, these osteogenic proteins induce formation of new bone in: large segmental bone defects, spinal fusions, and fractures. Without exception, each of the above-referenced disclosures describes implantation or delivery of the osteogenic protein at the defect site by packing, filling, and/or wrapping the defect site with an admixture of osteogenic protein and matrix, with the relative volume and surface area of matrix being significant. In the case of non-union defects which do not heal spontaneously, it has heretofore been conventional practice to implant volumes of matrix-osteogenic factor admixtures at the defect site, the volumes being sufficient to fill the defect in order to provide a 3-dimensional scaffold for subsequent new bone formation. While standard bone fractures, can heal spontaneously and without treatment, to the extent the art has contemplated treating fractures with osteogenic proteins, it has been the practice in the art to provide the osteogenic protein together with a matrix locally to a defect site to promote healing.

While implanting a volume of matrix may be conventional wisdom, particularly in the case of non-healing non-union defects, clinical consequences may develop in certain patients as a result of this practice. For example, patients undergoing repeated constructions or defect repairs, or wherein the matrix volume is large, can develop adverse immunologic reactions to matrices derived from collagen. Collagen matrices can be purified, but residual levels of contaminants can remain which is strongly allergenic for certain patients. Alternatively, demineralized autogenic, allogenic or xenogenic bone matrix can be used in place of collagen. Such a matrix is mechanically superior to collagen and can obviate adverse immune reactions in some cases, but proper preparation is expensive, time consuming and availability of reliable sources for bone may be limited. Such naturally-sourced matrices can be replaced with inert materials such as plastic, but plastic is not a suitable substitute since it does not resorb and is limited to applications requiring simple geometric configurations. To date, biodegradable polymers and copolymers have also been used as matrices admixed with osteogenic proteins for repair of non-union defects. While such matrices may overcome some of the above-described insufficiencies, use of these matrices still necessitates determination and control of features such as polymer chemistry, particle size, biocompatability and other particulars critical for operability.

In addition, individuals who, due to an acquired or congenital condition, have a reduced ability to heal bone fractures or other defects that normally undergo spontaneous repair would benefit from methods and injectable compositions that can enhance bone and/or cartilage repair without requiring a surgical procedure. Finally, an injectable formulation also provides means for repairing osteochondral or chondral defects without requiring a surgical procedure.

Needs remain for devices, implants and methods of repairing bone defects which do not rely on a matrix component. Particular needs remain for devices, implants and methods which permit delivery of bone-inducing amounts of osteogenic proteins without concomitant delivery of space-filling matrix materials which can compromise the recipient and/or fail to be biomechanically and torsionally ideal. Needs also remain for providing methods and devices, particularly injectable devices that can accelerate the rate and enhance the quality of new bone formation.

Accordingly, it is an object of the instant invention to provide devices, implants and methods of use thereof for repairing bone defects, cartilage defects and/or osteochondral defects which obviate the need for an admixture of osteogenic protein with matrix. The instant invention provides matrix-free osteogenic devices, implants and methods of use thereof for repairing non-healing non-union defects, as well as for promoting enhanced bone formation for spinal fusions and bone fractures, and for promoting articular cartilage repair in chondral or osteochondral defects. These and other objects, along with advantages and features of the invention disclosed herein, will be apparent from the description, drawings and claims that follow.

SUMMARY OF THE INVENTION

The present invention is based on the discovery that an osteogenic or bone morphogenic protein such as OP-1, alone or when admixed with a suitable carrier and not with a conventional matrix material, can induce endochondral bone formation sufficient to repair critical-sized, segmental bone defects. Thus this discovery overcomes the above-described problems associated with conventional materials and methods for repairing bone defects because it permits elimination of matrix material. Furthermore, in view of existing orthopedic and reconstructive practices, this discovery is unexpected and contravenes the art's current understanding of the bone repair/formation processes.

As disclosed herein, it is now appreciated that an osteogenic protein can be admixed with a carrier as defined herein to form a matrix-free device which, when provided to a mammal, is effective to promote repair of non-union bone defects, fractures and fusions. As disclosed herein, methods and devices are provided for inducing new bone formation at a local defect site without the need for also providing a three-dimensional structural component at the defect site. As contemplated herein, a "matrix-free" osteogenic device is a device devoid of matrix at the time it is provided to a recipient. It is understood that the term "matrix" means a structural component or substrate having a three-dimensional form and upon which certain cellular events involved in endochondral bone morphogenesis will occur; a matrix acts as a temporary scaffolding structure for infiltrating cells having interstices for attachment, proliferation and differentiation of such cells.

The invention provides, in one aspect therefore, a novel method for inducing bone formation in a mammal sufficient to repair a defect. One embodiment comprises the step of providing a matrix-free osteogenic device to a defect locus defining a void. The matrix-free device may be composed of osteogenic protein alone, or it may be composed of osteogenic protein in admixture with a biocompatible, amorphous non-rigid carrier having no defined surfaces. This method induces new bone formation which fills the defect locus, thereby repairing the defect. As contemplated herein, the method comprises providing a matrix-free osteogenic device to a defect locus, wherein the device is provided in a volume insufficient to fill the void at the defect locus. In certain embodiments, the void comprises a volume incapable of endogenous or spontaneous repair. Examples of defects suitable for repair by the instant method include, but are not limited to, critical-sized segmental defects and non-union fractures.

In another embodiment, the invention provides methods and compositions for enhancing fracture repair by providing the matrix-free osteogenic devices described herein to a fracture defect site. The ability of the devices described herein to substantially enhance fracture repair, including accelerating the rate and enhancing the quality of newly formed bone, has implications for improving bone healing in compromised individuals such as diabetics, smokers, obese individuals and others who, due to an acquired or congenital condition have a reduced capacity to heal bone fractures, including individuals with impaired blood flow to their extremities.

In another aspect, the invention provides an implant for inducing bone formation in a mammal sufficient to repair a defect. One preferred implant comprises a matrix-free osteogenic device disposed at a defect locus defining a void. Practice of the above-described method, i.e., providing an osteogenic device devoid of scaffolding structure to a mammal at a defect locus, results in an implant competent to induce new bone formation sufficient to promote repair of non-union bone defects, fractures and fusions. Upon disposition of the osteogenic device at the defect locus, the implant so formed has insufficient volume to fill the defect void.

In yet another aspect, the present invention provides a matrix-free osteogenic device for inducing bone formation in a mammal. As contemplated herein, a preferred osteogenic device comprises an osteogenically-active protein dispersed in a suitable carrier. Preferred osteogenic proteins, include but are not limited to, OP-1, OP-2, BMP-2, BMP-4, BMP-5, and BMP-6 (see below). As disclosed herein, preferred carriers are biocompatible, nonrigid and amorphous, having no defined surfaces or three-dimensional structural features. Thus, the devices of the instant invention lack scaffolding structure and are substantially free of matrix when administered to a mammal. Examples of preferred carriers include, but are not limited to, pluronics and alkylcelluloses. As discussed above, the method of the instant invention involves providing such a device to a defect locus such that the volume of the device is insufficient to fill the void volume at the defect locus.

The methods, implants and devices of the invention also are competent to induce and promote or enhance repair of chondral or osteochondral defects. As a result of this discovery means now are available for promoting bone and/or cartilage repair without requiring a surgical procedure. Particularly as a method for enhancing bone fracture repair, it is contemplated that a suitable formulation can be injected to a fracture site at the time the fracture is set so as to accelerate the rate and enhance the quality of new bone formation.

The device of the instant invention can have a variety of configurations. The nature of the device will be dependent upon the type of carrier in which the osteogenic protein is dispersed. For example, one preferred embodiment can have a paste-like or putty-like configuration; such a device can result from dispersing osteogenic protein in a gel-like carrier such as a "Pluronic" carrier or an alkylcellulose such as carboxymethyl cellulose which is then wetted with a suitable wetting agent such as, for example, a saline solution. Another preferred embodiment can have a dry powder configuration; such a device results from first dispersing osteogenic protein in a liquid carrier such as water with or without excipient, followed by lyophilization. A third formulation is a solution, such as by combining the protein together with an acidic buffered solution, e.g., pH 4.0–4.5, for example an acetate or citrate buffer. Still another formulation is a suspension formed by disbursing osteogenic protein in a physiologically buffered solution, such as phosphate buffered saline (PBS). Depending upon the configuration of the device, providing it to a defect locus can be accomplished by a variety of delivery processes. For example, a paste can be extruded as a bead which lays along one surface of the defect locus. Alternatively, a viscous liquid can be brushed or painted along one or more surfaces of the defect locus or injected through a wide gauge needle. Less viscous fluids can be injected through a fine gauge needle. Other configurations and modes of delivery are contemplated and discussed below in more detail.

Generally, the proteins of the invention are dimeric proteins that induce endochondral bone morphogenesis. Osteogenic proteins comprise a pair of polypeptides that, when folded, adopt a configuration sufficient for the resulting dimeric protein to elicit a morphogenetic response. That is, osteogenic proteins generally induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. Progenitor cells are uncommitted cells that are competent to differentiate into one or more specific types of differentiated cells, depending on their genomic repertoire and the tissue specificity of the permissive environment in which morphogenesis is induced. In the instant invention, osteogenic proteins can induce the morphogenic cascade which typifies endochondral bone formation.

As used herein, the term "morphogen", "bone morphogen", "bone morphogenic protein", "BMP", "osteogenic protein" and "osteogenic factor" embraces the class of proteins typified by human osteogenic protein 1 (hOP-1). Nucleotide and amino acid sequences for hOP-1 are provided in Seq. ID Nos. 1 and 2, respectively. For ease of description, hOP-1 is recited herein below as a representative osteogenic protein. It will be appreciated by the artisan of ordinary skill in the art, however, that OP-1 merely is representative of the TGF-β subclass of true tissue morphogenes competent to act as osteogenic proteins, and is not intended to limit the description. Other known, and useful proteins include, BMP-2, BMP-3, BMP-3b, BMP-4, BMP-5, BMP-6, BMP-8, BMP-9, BMP-10, BMP-11, BMP-12, BMP-13, BMP-15, GDF-1, GDF-2, GDF-3, GDF-5, GDF-6, GDF-7, GDF-8, GDF-9, GDF-10, GDF-11, GDF-12, NODAL, UNIVIN, SCREW, ADMP, NURAL and osteogenically active amino acid variants thereof. In one preferred embodiment, the proteins useful in the invention include biologically active species variants of any of these proteins, including conservative amino acid sequence variants, proteins encoded by degenerate nucleotide sequence variants, and osteogenically active proteins sharing the conserved seven cysteine skeleton as defined herein and encoded by a DNA sequence competent to hybridize to a DNA sequence encoding an osteogenic protein disclosed herein. In still another embodiment, useful osteogenic proteins include those sharing the conserved seven cysteine domain and sharing at least 70% amino acid sequence homology (similarity) within the C-terminal active domain, as defined herein.

In still another embodiment, the osteogenic proteins of the invention can be defined as osteogenically active proteins having any one of the generic sequences defined herein, including OPX and Generic Sequences 7 (SEQ ID NO:4) and 8 (SEQ ID NO:5) or Generic Sequences 9 (SEQ ID NO: 8) and 10 (SEQ ID NO:7). OPX accommodates the homologies between the various species of the osteogenic OP1 and OP2 proteins, and is described by the amino acid sequence presented herein below and in Seq. ID No. 3. Generic sequence 9 (SEQ ID NO: 8) is a 102 amino acid sequence containing the six cysteine skeleton defined by hOP1 (residues 330–431 of Seq. ID No. 2) and wherein the remaining residues accommodate the homologies of OP1, OP2, OP3, BMP-2, BMP-3, BMP-4, BMP-5, BMP-6, BMP-8, BMP-9, BMP-10, BMP-11, BMP-15, GDF-1, GDF-3, GDF-5, GDF-6, GDF-7, GDF-8, GDF-9, GDF-10, GDF-11, UNIVIN, NODAL, DORSALIN, NURAL, SCREW and ADMP. That is, each of the non-cysteine residues is independently selected from the corresponding residue in this recited group of proteins. Generic sequence 10 (SEQ ID NO: 7) is a 97 amino acid sequence containing the seven cysteine skeleton defined by hOP1 (335–431 Seq. ID No. 2) and wherein the remaining residues accommodate the homologies of the above-recited protein group.

As contemplated herein, this family of osteogenic proteins includes longer forms of a given protein, as well as phylogenetic, e.g., species and allelic variants and biosynthetic mutants, including C-terminal addition and deletion mutants and variants, such as those which may alter the conserved C-terminal cysteine skeleton, provided that the alteration still allows the protein to form a dimeric species having a conformation capable of inducing bone formation in a mammal when implanted in the mammal. In addition, the osteogenic proteins useful in this invention may include forms having varying glycosylation patterns and varying N-termini, may be naturally occurring or biosynthetically derived, and may be produced by expression of recombinant DNA in procaryotic or eucaryotic host cells. The proteins are active as a single species (e.g., as homodimers), or combined as a mixed species, including heterodimers.

The methods and implants of the invention do not require a carrier for the osteogenic protein to induce bone formation sufficient to fill a critical size bone defect or to enhance fracture repair in an animal. When the protein is provided in association with a carrier in the practice of the invention, the carrier must lack a scaffolding structure, as stated above. When a preferred carrier is admixed with an osteogenic protein, a device is formed which is substantially free of matrix as defined herein. "Substantially free of matrix" is understood to mean that, the carrier-containing device as formulated prior to administration, does not contain a substrate competent to act as a scaffold per se. That is, the device contains no substrate which has been introduced from an exogenous source and is competent to act as a scaffold. Stated another way, prior to delivery, the carrier is recognized, by virtue of its chemical nature, to be unable to contribute a scaffolding structure to the device. By definition, preferred carriers are biocompatible, non-rigid and amorphous, having no defined surfaces. As used herein, "non-rigid" means a carrier formulation that is lax or pliant or otherwise is substantially incapable of providing or forming a three-dimensional structure having one or more defined surfaces. As used herein, "amorphous" means lacking a definite three-dimensional form, or specific shape, that is, having no particular shape or form, or having an indeterminate shape or form. Preferred carriers are also biocompatible, non-particulate, adherent to bone, cartilage and/or muscle, and inert. In certain embodiments, water-soluble carriers are preferable. Additionally, preferred carriers do not contribute significant volume to a device of the instant invention. That is, a preferred carrier permits dispersal of an osteogenic protein such that the final volume of the resulting device is less than the volume of the void at the defect locus. As discussed below, a preferred carrier can be a gel, an aqueous solution, a suspension or a viscous liquid. For example, particularly preferred carriers can include, without limitation, poloxamers, alkylcelluloses, acetate buffers, physiological saline solutions, lactose, mannitol and/or other sugars. Alternatively, osteogenic proteins can be provided alone to a defect site.

In summary, the methods, implants and devices of the present invention can be used to induce endochondral and intramembranous bone formation sufficient to repair bone defects which do not heal spontaneously, as well as to promote and enhance the rate and/or quality of new bone formation, particularly in the repair of fractures and fusions, including spinal fusions. The methods, implants and devices also are competent to induce repair of osteochondral and/or subchondral defects. That is, the methods, implants and devices are competent to induce formation of new bone and the overlying surface cartilage. The present invention is particularly suitable for use in collagen- or matrix-allergenic recipients. It is also particularly suitable for use in patients requiring repetitive reconstructive surgeries, as well as cancer patients as an alternative to reconstructive procedures using metal joints. The present invention also is useful for individuals whose ability to undergo spontaneous bone repair is compromised, such as diabetics, smokers, obese individuals, immune-compromised individuals, and any individuals have reduced blood flow to their extremities. Other applications include, but are not limited to, prosthetic repair, spinal fusion, scoliosis, cranial/facial repair, and massive allograft repair.

DETAILED DESCRIPTION OF PREFERRED EMBODIMENTS

In order to more clearly and concisely describe the subject matter of the claimed invention, the following definitions are intended to provide guidance as to the meaning of specific terms used in the following written description and appended claims.

"Bone formation" means formation of endochondral bone or formation of intramembranous bone. In humans, bone formation begins during the first 6–8 weeks of fetal development. Progenitor stem cells of mesenchymal origin migrate to predetermined sites, where they either: (a) condense, proliferate, and differentiate into bone-forming cells (osteoblasts), a process observed in the skull and referred to as "intramembranous bone formation;" or, (b) condense, proliferate and differentiate into cartilage-forming cells (chondroblasts) as intermediates, which are subsequently replaced with bone-forming cells. More specifically, mesenchymal stem cells differentiate into chondrocytes. The chondrocytes then become calcified, undergo hypertrophy and are replaced by newly formed bone made by differentiated osteoblasts which now are present at the locus. Subsequently, the mineralized bone is extensively remodeled, thereafter becoming occupied by an ossicle filled with functional bone-marrow elements. This process is observed in long bones and referred to as "endochondral bone formation." In postfetal life, bone has the capacity to repair itself upon injury by mimicking the cellular process of embryonic endochondral bone development. That is, mesenchymal progenitor stem cells from the bone-marrow, periosteum, and muscle can be induced to migrate to the defect site and begin the cascade of events described above. There, they accumulate, proliferate, and differentiate into cartilage which is subsequently replaced with newly formed bone.

"Defect" or "defect locus" as contemplated herein defines a void which is a bony structural disruption requiring repair. The defect further can define an osteochondral defect, including both a structural disruption of the bone and overlying cartilage. "Void" is understood to mean a three-dimensional defect such as, for example, a gap, cavity, hole or other substantial disruption in the structural integrity of a bone or joint. A defect can be the result of accident, disease, surgical manipulation and/or prosthetic failure. In certain embodiments, the defect locus is a void having a volume incapable of endogenous or spontaneous repair. Such defects are also called critical-sized segmental defects. The art recognizes such defects to be approximately 3–4 cm, at least greater than 2.5 cm, gap incapable of spontaneous repair. In other embodiments, the defect locus is a non-critical segmental defect approximately at least 0.5 cm but not more than approximately 2.5 cm. Generally, these are capable of some spontaneous repair, albeit biomechanically inferior to that made possible by practice of the instant innovation. In certain other embodiments, the defect is an osteochondral defect such as an osteochondral plug. Other defects susceptible to repair using the instant invention include, but are not limited to, non-union fractures; bone cavities; tumor resection; fresh fractures; cranial/facial abnormalities; spinal fusions, as well as those resulting from diseases such as cancer, arthritis, including osteoarthritis, and other bone degenerative disorders. "Repair" is intended to mean induction of new bone formation which is sufficient to fill the void at the defect locus, but "repair" does not mean or otherwise necessitate a process of complete healing or a treatment which is 100% effective at restoring a defect to its pre-defect physiological/structural state.

"Matrix" is understood in the art to mean an osteoconductive substrate having a scaffolding structure on which infiltrating cells can attach, proliferate and participate in the morphogenic process culminating in bone formation. In certain embodiments, matrix can be particulate and porous, with porosity being a feature critical to its effectiveness in inducing bone formation, particularly endochondral bone formation. As described earlier, a matrix is understood to provide certain structural components to the conventional osteogenic device (i.e., heretofore comprising a porous, particulate matrix component such as collagen, demineralized bone or synthetic polymers), thereby acting as a temporary and resorbable scaffolding structure for infiltrating cells having interstices for attachment, proliferation and differentiation of such cells. Accordingly, the term "matrix-free osteogenic device" or an osteogenic device which is "substantially free of matrix" contemplates a device which is devoid of an art-recognized matrix at the time it is provided to a recipient. Moreover, substantially free of matrix is understood to mean that, when a device is provided to a defect locus, no substrate competent to act as a scaffold per se is introduced from an exogenous source. Matrix-free or substantially free of matrix is not intended to exclude endogenous matrix which is induced or formed following delivery of the devices and/or implants disclosed herein to a defect locus. Thus the present invention further contemplates a method of inducing endogenous matrix formation by providing to a defect locus the matrix-free devices or implants disclosed herein.

"Osteogenic device" is understood to mean a composition comprising osteogenic protein dispersed in a biocompatible, non-rigid amorphous carrier having no defined surfaces. Osteogenic devices of the present invention are competent to induce bone formation sufficient to fill a defect locus defining a void. Osteogenic devices are matrix-free when provided to the defect locus and are delivered to the defect locus in a volume insufficient to fill the void defined by the defect locus. A device can have any suitable configuration, such as liquid, powder, paste, or gel, to name but a few. Preferred properties of osteogenic devices suitable for use with the method of the instant invention include, but are not limited to: adherent to bone, cartilage and/or muscle; and, effective to provide at least a local source of osteogenic protein at the defect locus, even if transient. As contemplated herein, providing a local source of protein includes both retaining protein at the defect locus as well as controlled release of protein at the defect locus. All that is required by the present invention is that the osteogenic device be effective to deliver osteogenic protein at a concentration sufficient to induce bone formation that fills the three-dimensional defect defining the void requiring repair. In addition to osteogenic proteins, various growth factors, hormones, enzymes therapeutic compositions, antibiotics, or other bioactive agents can also be contained within an osteogenic device. Thus, various known growth factors such as EGF, PDGF, IGF, FGF, TGF-$\alpha$, and TGF-$\beta$ can be combined with an osteogenic device and be delivered to the defect locus. An osteogenic device can also be used to deliver chemotherapeutic agents, insulin, enzymes, enzyme inhibitors and/or chemoattractant/chemotactic factors.

"Osteogenic protein" or bone morphogenic protein is generally understood to mean a protein which can induce the full cascade of morphogenic events culminating in endochondral bone formation. As described elsewhere herein, the class of proteins is typified by human osteogenic protein (hOP 1). Other osteogenic proteins useful in the practice of the invention include osteogenically active forms of OP 1, OP2, OP3, BMP2, BMP3, BMP4, BMP5, BMP6, BMP9, DPP, Vg1, Vgr, 60A protein, GDF-1, GDF-3, GDF-5, 6, 7, BMP10, BMP11, BMP13, BMP15, UNIVIN, NODAL, SCREW, ADNT or NURAL and amino acid sequence variants thereof. In one currently preferred embodiment, osteogenic protein include any one of: OP1, OP2, OP3, BMP2, BMP4, BMP5, BMP6, BMP9, and amino acid sequence variants and homologs thereof, including species homologs, thereof. Particularly preferred osteogenic proteins are those comprising an amino acid sequence having at least 70% homology with the C-terminal 102–106 amino acids, defining the conserved seven cystein domain, of human OP-1, BMP2, and related proteins. Certain preferred embodiments of the instant invention comprise the osteogenic protein, OP-1. Certain other preferred embodiments comprise mature OP-1 solubilized in a physiological saline solution. As further described elsewhere herein, the osteogenic proteins suitable for use with Applicants' invention can be identified by means of routine experimentation using the art-recognized bioassay described by Reddi and Sampath. "Amino acid sequence homology" is understood herein to mean amino acid sequence similarity. Homologous sequences share identical or similar amino acid residues, where similar residues are conservative substitutions for, or allowed point mutations of, corresponding amino acid residues in an aligned reference sequence. Thus, a candidate polypeptide sequence that shares 70% amino acid homology with a reference sequence is one in which any 70% of the aligned residues are either identical to or are conservative substitutions of the corresponding residues in a reference sequence. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Proteins useful in this invention include eukaryotic proteins identified as osteogenic proteins (see U.S. Pat. No. 5,011,691, incorporated herein by reference), such as the OP-1, OP-2, OP-3 and CBMP-2 proteins, as well as amino acid sequence-related proteins such as DPP (from Drosophila), Vg1 (from Xenopus), Vgr-1 (from mouse), GDF-1 (from humans, see Lee (1991), *PNAS* 88:4250–4254), 60A (from Drosophila, see Wharton et al. (1991) *PNAS* 88:9214–9218), dorsalin-1 (from chick, see Basler et al. (1993) *Cell* 73:687–702 and GenBank accession number L12032) and GDF-5 (from mouse, see Storm et al. (1994) *Nature* 368:639–643). BMP-3 is also preferred. Additional useful proteins include biosynthetic morphogenic constructs disclosed in U.S. Pat. No. 5,011,691, e.g., COP-1, 3–5, 7 and 16, as well as other proteins known in the art. Still other proteins include osteogenically active forms of BMP-3b (see Takao, et al., (1996), *Biochem. Biophys. Res. Comm.* 219: 656–662. BMP-9 (see WO95/33830), BMP-15 (see WO96/35710), BMP-12 (see WO95/16035), CDMP-1 (see WO94/12814), CDMP-2 (see WO94/12814), BMP-10 (see WO94/26893), GDF-1 (see WO92/00382), GDF-10 (see WO95/10539), GDF-3 (see WO94/15965) and GDF-7 (WO95/01802).

Still other useful proteins include proteins encoded by DNAs competent to bybridize to a DNA encoding an osteogenic protein as described herein, and related analogs, homologs, muteins and the like (see below).

"Carrier" as used herein means a biocompatible, non-rigid, amorphous material having no defined surfaces suitable for use with the devices, implants and methods of the present invention. As earlier stated, "non-rigid" means a carrier formulation that is lax or pliant or otherwise is substantially incapable of providing or forming a three-dimensional structure having one or more defined surfaces. As used herein, "amorphous" means lacking a definite three-dimensional form, or specific shape, that is, having no particular shape or form, or having an indeterminate shape or form. Suitable carriers also are non-particulate and are non- porous, i.e., are pore-less. Carriers suitable for use in the instant invention lack a three-dimensional scaffolding structure and are substantially matrix-free. Thus, "substantially free of matrix" is also understood to mean that, when a carrier-containing device is provided to a defect locus, no substrate competent to act as a scaffold per se is introduced from any exogenous source, including the carrier. Prior to delivery to and implantation in the recipient, the carrier is recognized by virtue of its chemical nature to be unable to contribute a three-dimensional scaffolding structure to the device. Preferred carriers are adherent, at least transiently, to tissues such as bone, cartilage and/or muscles. Certain preferred carriers are water-soluble, viscous, and/or inert.

Additionally, preferred carriers do not contribute significant volume to a device. Currently preferred carriers include, without limitation alkylcelluloses, poloxamers, gelatins, polyethylene glycols, dextrins, vegetable oils and sugars. Particularly preferred carriers currently include but are not limited to poloxamer 407, carboxymethylcelluloses, lactose, mannitol and sesame oil. Other preferred carriers include acetate buffer (20 mM, pH 4.5), physiological saline (PBS), and citrate buffer. In the case of devices comprising carriers such as acetate, poloxamers and PBS, administration by injection can result in precipitation of certain osteogenic proteins at the administration site.

"Implant" as contemplated herein comprises osteogenic protein dispersed in a biocompatible, nonrigid amorphous carrier having no defined surfaces disposed at a defect locus defining a void. That is, the implant of the present invention is contemplated to comprise the defect locus per se into/onto which the device of the present invention has been delivered/deposited. It is further contemplated that, at the time of delivery of a device, an implant lacks scaffolding structure and is substantially matrix-free. Implants resulting from practice of the instant method are competent to induce bone formation in a defect locus in a mammal sufficient to fill the defect with newly formed bone without also requiring inclusion of a matrix or scaffolding structure, at the time of delivery of a device, sufficient to substantially fill the void thereby structurally defining the defect size and shape.

The means for making and using the methods, implants and devices of the invention, as well as other material aspects concerning their nature and utility, including how to make and how to use the subject matter claimed, will be further understood from the following, which constitutes the best mode currently contemplated for practicing the invention. It will be appreciated that the invention is not limited to such exemplary work or to the specific details set forth in these examples.

I. PROTEIN CONSIDERATIONS

A. Biochemical, Structural and Functional Properties of Bone Morphogenic Proteins Naturally occurring proteins identified and/or appreciated herein to be osteogenic or bone morphogenic proteins form a distinct subgroup within the loose evolutionary grouping of sequence-related proteins known as the TGF-β superfamily or supergene family. The naturally occurring bone morphogens share substantial amino acid sequence homology in their C-terminal regions (domains). Typically, the above-mentioned naturally occurring osteogenic proteins are translated as a precursor, having an N-terminal signal peptide sequence, typically less than about 30 residues, followed by a "pro" domain that is cleaved to yield the mature C-terminal domain. The signal peptide is cleaved rapidly upon translation, at a cleavage site that can be predicted in a given sequence using the method of Von Heijne (1986) *Nucleic Acids Research* 14:4683–4691. The pro domain typically is about three times larger than the fully processed mature C-terminal domain. Herein, the "pro" form of a morphogen refers to a morphogen comprising a folded pair of polypeptides each comprising the pro and mature domains of a morphogen polypeptide. Typically, the pro form of a morphogen is more soluble than the mature form under physiological conditions. The pro form appears to be the primary form secreted from cultured mammalian cells.

In preferred embodiments, the pair of morphogenic polypeptides have amino acid sequences each comprising a sequence that shares a defined relationship with an amino acid sequence of a reference morphogen. Herein, preferred osteogenic polypeptides share a defined relationship with a sequence present in osteogenically active human OP-1, SEQ ID NO: 2. However, any one or more of the naturally occurring or biosynthetic sequences disclosed herein similarly could be used as a reference sequence. Preferred osteogenic polypeptides share a defined relationship with at least the C-terminal six cysteine domain of human OP-1, residues 335–431 of SEQ ID NO: 2. Preferably, osteogenic polypeptides share a defined relationship with at least the C-terminal seven cysteine domain of human OP-1, residues 330–431 of SEQ ID NO: 2. That is, preferred polypeptides in a dimeric protein with bone morphogenic activity each comprise a sequence that corresponds to a reference sequence or is functionally equivalent thereto.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. Functionally equivalent sequences further include a those wherein one or more amino acid residues differs from the corresponding residue of a reference sequence, e.g., the C-terminal seven cysteine domain (also referred to herein as the conserved seven cysteine skeleton) of human OP-1, provided that this difference does not destroy bone morphogenic activity. Accordingly, conservative substitutions of corresponding amino acids in the reference sequence are preferred. Amino acid residues that are conservative substitutions for corresponding residues in a reference sequence are those that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an accepted point mutation in Dayhoff et al. (1978), 5 *Atlas of Protein Sequence and Structure*, Suppl. 3, ch. 22 (pp. 354–352), Natl. Biomed. Res. Found., Washington, D.C. 20007, the teachings of which are incorporated by reference herein.

Natural-sourced osteogenic protein in its mature, native form is a glycosylated dimer typically having an apparent molecular weight of about 30–36 kDa as determined by SDS-PAGE. When reduced, the 30 kDa protein gives rise to two glycosylated peptide subunits having apparent molecular weights of about 16 kDa and 18 kDa. In the reduced state, the protein has no detectable osteogenic activity. The unglycosylated protein, which also has osteogenic activity, has an apparent molecular weight of about 27 kDa. When reduced, the 27 kDa protein gives rise to two unglycosylated polypeptides having molecular weights of about 14 kDa to 16 kDa capable of inducing endochondral bone formation in a mammal. As described above, particularly useful sequences include those comprising the C-terminal 102 amino acid sequences of DPP (from Drosophila), Vg1 (from Xenopus), Vgr-1 (from mouse), the OP1 and OP2 proteins, proteins (see U.S. Pat. No. 5,011,691 and Oppermann et al., as well as the proteins referred to as BMP2, BMP3, BMP4 (see WO88/00205, U.S. Pat. No. 5,013,649 and WO91/18098), BMP5 and BMP6 (see WO90/11366, PCT/US90/01630) and BMP8 and 9.

In certain preferred embodiments, bone morphogenic proteins useful herein include those in which the amino acid sequences comprise a sequence sharing at least 70% amino acid sequence homology or "similarity", and preferably 80% homology or similarity with a reference morphogenic protein selected from the foregoing naturally occurring proteins. Preferably, the reference protein is human OP-1, and the reference sequence thereof is the C-terminal seven cysteine domain present in osteogenically active forms of human OP-1, residues 330–431 of SEQ ID NO: 2. Bone morphogenic proteins useful herein accordingly include allelic, phylogenetic counterpart and other variants of the preferred reference sequence, whether naturally-occurring or biosynthetically produced (e.g., including "muteins" or "mutant proteins"), as well as novel members of the general morphogenic family of proteins including those set forth and identified above. Certain particularly preferred morphogenic polypeptides share at least 60% amino acid identity with the preferred reference sequence of human OP-1, still more preferably at least 65% amino acid identity therewith.

In other preferred embodiments, the family of bone morphogenic polypeptides useful in the present invention, and members thereof, are defined by a generic amino acid sequence. For example, Generic Sequence 7 (SEQ ID NO: 4) and Generic Sequence 8 (SEQ ID NO: 5) disclosed below, accommodate the homologies shared among preferred protein family members identified to date, including at least OP-1, OP-2, OP-3, CBMP-2A, CBMP-2B, BMP-3, 60A, DPP, Vg1, BMP-5, BMP-6, Vgr-1, and GDF-1. The amino acid sequences for these proteins are described herein and/or in the art, as summarized above. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences provide an appropriate cysteine skeleton where inter- or intramolecular disulfide bonds can form, and contain certain critical amino acids likely to influence the tertiary structure of the folded proteins. In addition, the generic sequences allow for an additional cysteine at position 41 (Generic Sequence 7) or position 46 (Generic Sequence 4), thereby encompassing the morphogenically active sequences of OP-2 and OP-3.

(SEQ ID NO:4)
Generic Sequence 7

```
            Leu Xaa Xaa Xaa Phe Xaa Xaa
             1               5

Xaa Gly Trp Xaa Xaa Xaa Xaa Xaa Xaa Pro
    10                  15

Xaa Xaa Xaa Xaa Ala Xaa Tyr Cys Xaa Gly
    20                  25

Xaa Cys Xaa Xaa Pro Xaa Xaa Xaa Xaa Xaa
    30                  35

Xaa Xaa Xaa Asn His Ala Xaa Xaa Xaa Xaa
    40                  45

Xaa Xaa Xaa Xaa Xaa Xaa Xaa Xaa Xaa Xaa
    50                  55

Xaa Xaa Xaa Cys Cys Xaa Pro Xaa Xaa Xaa
    60                  65

Xaa Xaa Xaa Xaa Xaa Leu Xaa Xaa Xaa Xaa
    70                  75
```

-continued (SEQ ID NO:4)
Generic Sequence 7

```
Xaa Xaa Xaa Val Xaa Leu Xaa Xaa Xaa Xaa
    80                  85

Xaa Met Xaa Val Xaa Xaa Cys Xaa Cys Xaa
    90                  95
```

wherein each Xaa pendently is selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp or Glu); Xaa at res.8=(Leu, Val or Ile); Xaa at res.11=(Gln, Leu, Asp, His, Asn or Ser); Xaa at res.12=(Asp, Arg, Asn or Glu); Xaa at res.13=(Trp or Ser); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Ty or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln, Ala or Ser); Xaa at res.28=(Glu, Lys, Asp, Gln or Ala); Xaa at res.30=(Ala, Ser, Pro, Gln, Ile or Asn); Xaa at res.31=(Phe, Leu, or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40=(Thr, Leu or Ser); Xaa at res.44=(Ile, Val or Thr); Xaa at res.45=(Val, Leu, Met or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val, Gly or Leu); Xaa at res.53=(Asn, Lys, Ala, Glu, Gly or Phe); Xaa at res.54=(Pro, Ser or Val); Xaa at res.55=(Glu, Asp, Asn, Gly, Val, Pro or Lys); Xaa at res.56=(Thr, Ala, Val, Lys, Asp, Tyr, Ser, Gly, Ile or His); Xaa at res.57=(Val, Ala or Ile); Xaa at res.58=(Pro or Asp); Xaa at res.59=(Lys, Leu or Glu); Xaa at res.60=(Pro, Val or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Leu, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn, Arg or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His, Arg or Val); Xaa at res.86=(Tyr, Glu or His); Xaa at res.87=(Arg, Gln, Glu or Pro); Xaa at res.88=(Asn, Glu, Trp or Asp); Xaa at res.90=(Val, Thr, Ala or Ile); Xaa at res.92=(Arg, Lys, Val, Asp, Gln or Glu); Xaa at res.93=(Ala, Gly, Glu or Ser); Xaa at res.95=(Gly or Ala) and Xaa at res.97=(His or Arg).

Generic Sequence 8 (SEQ ID NO: 5) includes all of Generic Sequence 7 (SEQ ID NO:4) and in addition includes the following sequence (SEQ ID NO: 6) at its N-terminus:

Accordingly, beginning with residue 7, each "Xaa" in Generic Sequence 8 (SEQ ID NO:5) is a specified amino acid defined as for Generic Sequence 7 (SEQ ID NO:4), with the distinction that each residue number described for Generic Sequence 7 (SEQ ID NO:4) is shifted by five in Generic Sequence 8 (SEQ ID NO:5). Thus, "Xaa at res.2=

(Tyr or Lys)" in Generic Sequence 7 (SEQ ID NO:4) refers to Xaa at res. 7 in Generic Sequence 8 (SEQ ID NO:5). In Generic Sequence 8 (SEQ ID NO:5), Xaa at res.2=(Lys, Arg, Ala or Gln); Xaa at res.3=(Lys, Arg or Met); Xaa at res.4=(His, Arg or Gln); and Xaa at res.5=(Glu, Ser, His, Gly, Arg, Pro, Thr, or Tyr).

In another embodiment, useful osteogenic proteins include those defined by Generic Sequences 9 (SEQ ID NO:8) and 10 (SEQ ID NO:7), described herein above.

As noted above, certain currently preferred bone morphogenic polypeptide sequences useful in this invention have greater than 60% identity, preferably greater than 65% identity, with the amino acid sequence defining the preferred reference sequence of hOP-1. These particularly preferred sequences include allelic and phylogenetic counterpart variants of the OP-1 and OP-2 proteins, including the Drosophila 60A protein. Accordingly, in certain particularly preferred embodiments, useful morphogenic proteins include active proteins comprising pairs of polypeptide chains within the generic amino acid sequence herein referred to as "OPX" (SEQ ID NO: 3), which defines the seven cysteine skeleton and accommodates the homologies between several identified variants of OP-1 and OP-2. As described therein, each Xaa at a given position independently is selected from the residues occurring at the corresponding position in the C-terminal sequence of mouse or human OP-1 or OP-2.

In still another preferred embodiment, useful osteogenically active proteins have polypeptide chains with amino acid sequences comprising a sequence encoded by nucleic acid that hybridizes, under low, medium or high stringency hybridization conditions, to DNA or RNA encoding reference morphogen sequences, e.g., C-terminal sequences defining the conserved seven cysteine domains of OP-1, OP-2, BMP2, 4, 5, 6, 60A, GDF3, GDF6, GDF7 and the like. As used herein, high stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringence conditions are well characterized in commercially available, standard molecular cloning texts.

As noted above, proteins useful in the present invention generally are dimeric proteins comprising a folded pair of the above polypeptides. Such morphogenic proteins are inactive when reduced, but are active as oxidized homodimers and when oxidized in combination with others of this invention to produce heterodimers. Thus, members of a folded pair of morphogenic polypeptides in a morphogenically active protein can be selected independently from any of the specific polypeptides mentioned above.

The bone morphogenic proteins useful in the materials and methods of this invention include proteins comprising any of the polypeptide chains described above, whether isolated from naturally-occurring sources, or produced by recombinant DNA or other synthetic techniques, and includes allelic and phylogenetic counterpart variants of these proteins, as well as biosynthetic variants (muteins) thereof, and various truncated and fusion constructs. Deletion or addition mutants also are envisioned to be active, including those which may alter the conserved C-terminal six or seven cysteine domain, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The bone morphogenic proteins contemplated herein can be expressed from intact or truncated cDNA or from synthetic DNAs in prokaryotic or eukaryotic host cells, and purified, cleaved, refolded, and dimerized to form morphogenically active compositions. Currently preferred host cells include *E. coli* or mammalian cells, such as CHO, COS or BSC cells. Detailed descriptions of the bone morphogenic proteins useful in the practice of this invention, including how to make, use and test them for osteogenic activity, are disclosed in numerous publications, including U.S. Pat. Nos. 5,266,683 and 5,011,691, the disclosures of which are incorporated by reference herein.

Thus, in view of this disclosure, skilled genetic engineers can isolate genes from cDNA or genomic libraries of various different biological species, which encode appropriate amino acid sequences, or construct DNAs from oligonucleotides, and then can express them in various types of host cells, including both prokaryotes and eukaryotes, to produce large quantities of active proteins capable of stimulating endochondial bone morphogenesis in a mammal.

B. Preparations of Bone Morphogenic Protein, OP-1

1. Lyophilized Protein

OP-1 can be lyophilized from 20 mM acetate buffer, pH 4.5, with 5% mannitol, lactose, glycine or other additive or bulking agent, using standard lyophilization protocols. OP-1 reconstituted in this manner has been observed to be biologically active for at least six months stored at 4° C. or 30° C.

OP-1 can also be lyophilized from a succinate or a citrate buffer (or other non-volatile buffer) for re-constitution in water, and from water for re-constitution in 20mM acetate buffer, pH 4.5. Generally, additives such as lactose, sucrose, glycine and mannitol are suitable for use in lyophilized matrix-free osteogenic devices. In certain embodiments, such devices (0.5 mg/ml OP-1 and 5% additive) can be prepared in a wet or dry configuration prior to lyophilization.

For example, liquid formulations of OP-1 in 10 and 20 mM acetate buffer (pH 4, 4.5 and 5) with and without mannitol (0%, 1% and 5%) are stable and osteogenically active for at least six months.

II. CARRIER CONSIDERATIONS

As already explained, "carrier" as used herein means a biocompatible, non-rigid, amorphous material having no defined surfaces suitable for use with the devices, implants and methods of the present invention. Suitable carriers are non-particulate and are non- porous, i.e., are pore-less. Carriers suitable for use in the instant invention lack a scaffolding structure and are substantially matrix-free. Thus, "substantially free of matrix" is also understood to mean that, when a carrier-containing device is provided to a defect locus, no substrate competent to act as a scaffold per se is introduced from an exogenous source, including the carrier. Prior to delivery to and implantation in the recipient, the carrier is recognized by virtue of its chemical nature to be substantially unable to contribute a three-dimensional scaffolding structure to the device. Preferred carriers are adherent, at least transiently, to tissues such as bone, cartilage and/or muscles. Certain preferred carriers are water-soluble, viscous, and/or inert. Additionally, preferred carriers do not contribute significant volume to a device. Currently preferred carriers are selected from the group consisting of: alkylcelluloses, poloxamers, gelatins, polyethylene glycols (PEG), dextrins, vegetable oils and sugars. Particularly preferred carriers currently include, but are not limited to, poloxamer 407, carboxymethylcelluloses (CMC), (e.g., low viscosity CMC from Aqualon), lactose, PEG, mannitol, sesame oil, and hetastarch (Hespan, Dupont), and combinations thereof. Other preferred carriers include, without limitation, acetate buffer (20 mM, pH 4.5), physiological saline, and citrate buffers. In the case of devices comprising carriers such as acetate, poloxamers and PBS, administration by injection can result in precipitation of certain osteogenic proteins at the administration site.

III. FORMULATION AND DELIVERY CONSIDERATIONS

The devices of the invention can be formulated using routine methods. All that is required is determining the desired final concentration of osteogenic protein per unit volume of carrier, keeping in mind that the delivered volume of device will be less than the volume the void at the defect locus. The desired final concentration of protein will depend on the specific activity of the protein as well as the type, volume, and/or anatomical location of the defect. Additionally, the desired final concentration of protein can depend on the age, sex and/or overall health of the recipient. Typically, for a critical-sized segmental defect approximately at least 2.5 cm in length, 0.05 ml (or mg) of a device containing 0.5–1.5 mg osteogenic protein has been observed to induce bone formation sufficient to repair the gap. In the case of a non-critical sized defect fresh fractures, approximately 0.1–0.5 mg protein has been observed to repair the gap or defect. Optimization of dosages requires no more than routine experimentation and is within the skill level of one of ordinary skill in the art.

As exemplified below, the devices of the present invention can assume a variety of configurations. For example, a matrix-free osteogenic device in solution can be formulated by solubilizing certain forms of OP-1 in solutions of acetate (20 mM, pH 4.5) or citrate buffers, or phosphate-buffered saline (PBS), pH 7.5. In some instances, the osteogenic protein may not be entirely solubilized and/or may precipitate upon administration into the defect locus. Suspensions, aggregate formation and/or in vivo precipitation does not impair the operativeness of the matrix-free osteogenic device when practiced in accordance with the invention disclosed herein. Matrix-free devices in solution are particularly suitable for administration by injection, such as providing a device to a fracture locus by injection rather than surgical means.

Generally speaking, the configuration of matrix-free devices suitable for delivery by injection differ from those preferred for use at an open, surgical site. For example, lyophilized preparations of matrix-free devices are one currently preferred embodiment for repair of this type of defect. The above-described matrix-free devices in solution can be used to prepare a lyophilized configuration. For example, as described below, the osteogenic protein OP-1 can be admixed with the above-described buffers and then lyophilized. OP-1 can also be lyophilized from mannitol-containing water.

As exemplified below, lyophilized configurations of matrix-free osteogenic devices can induce bone formation in critical-sized and non-critical sized segmental defects. For example, providing a lyophilized device to a segmental defect locus comprises depositing non-contiguous aliquots of the lyophilized device along the length of exposed muscle spanning the segmental defect, such that the total number of aliquots provides an amount of osteogenic protein sufficient to induce bone formation which ultimately fills the void at the defect locus. Placement is followed by routine closure of the defect site whereby the layers of muscles and associated tissue are sutured, layer-by-layer, to enclose the aliquots in the void at the defect locus. This type of delivery and surgical closure require only routine skill and experimentation. Similar formulations and methods of delivery can be used to induce bone formation for repair of a gap caused by a failed prosthetic, bone tumor resection, cranial/facial reconstruction, spinal fusions and massive allograft defects. Any modifications of the above-described methods of delivery which may be required for specialized applications of lyophilized matrix-free devices are within the skill level of the artisan and require only routine experimentation.

Yet another configuration of matrix-free devices is exemplified below. Osteogenic protein and a carrier such as carboxymethylcellulose (low viscosity, Aqualon, or poloxamer 407 can be admixed to form a paste. In some embodiments, approximately saline is added to carrier to form a paste into which an osteogenic protein such as OP-1 can be dispersed. A paste configuration can be used to paint the surfaces of a defect such as a cavity. Pastes can be used to paint fracture defects, chondral or osteochondral defects, as well as bone defects at a prosthetic implant site. A paste can also be injected or extruded into or along one of the surfaces of a defect, in a manner similar to extruding toothpaste or caulking from a tube, such that a bead of matrix-free device is delivered along the length of the defect locus. Typically, the diameter of the extruded bead is determined by the type of defect as well as the volume of the void at the defect locus.

Carriers such as carboxymethylcellulose can also be used to formulate a device with a configuration like putty. As will be obvious to the skilled artisan, such a configuration results from adjusting the proportion of carrier to wetting agent, with less wetting agent producing a drier device and more producing a wetter device. The precise device configuration suitable to repair a defect will at least depend on the type of defect and the size of the defect. The skilled artisan will appreciate the variables.

Yet another configuration which is suitable for the devices of the instant invention is a gel. This is exemplified below by the poloxamer-containing matrix-free devices which can induce bone formation in vivo. Gels of this type have been used to treat fractures as well as gap repairs. One useful feature of this configuration is that the viscosity of the gel can be manipulated by adjusting the amount of carrier, thereby permitting a wide-range of applications (e.g., segmental defects, fractures, and reconstructions) and modes of delivery (e.g., injection, painting, extrusion, and the like). Thus this type of device can assume at least the forms of an injectable liquid, a viscous liquid, and an extrudable gel merely by manipulating the amount of carrier into which the osteogenic protein is dispersed.

In yet other embodiments of the present invention, preparation of the actual osteogenic device can occur immediately prior to its delivery to the defect locus. For example, CMC-containing devices can be prepared on-site, suitable for admixing immediately prior to surgery. In one embodiment, low viscosity CMC (Aqualon) is packaged and irradiated separately from the osteogenic protein OP-1. The OP-1 protein then is admixed with the CMC carrier, and tested for osteogenic activity. Devices prepared in this manner were observed to be as biologically active as the conventional device without CMC. Again, all that is required is determining the effective amount of osteogenic protein to induce bone formation sufficient to fill the defect locus and maintaining a device volume which is less than the volume of the void at the defect locus. The precise manner in which the device of the present invention is formulated, and when or how formulation is accomplished, is not critical to operativeness.

Practice of the invention will be still more fully understood from the following examples, which are presented herein for illustration only and should not be construed as limiting the invention in any way.

IV. BIOASSAY

A. Bioassay of Osteogenic Activity: Endochondral Bone Formation and Related Properties The following sets forth protocols for identifying and characterizing bonafide osteogenic or bone morphogenic proteins as well as osteogenic devices within the scope of Applicants' invention.

The art-recognized bioassay for bone induction as described by Sampath and Reddi (Proc. Natl. Acad. Sci. U.S.A (1983) 80:6591–6595) and U.S. Pat. No. 4,968,590, the disclosures of which are herein incorporated by reference, is used to establish the efficacy of the purification protocols. As is demonstrated below, this assay consists of depositing the test samples in subcutaneous sites in allogeneic recipient rats under ether anesthesia. A vertical incision (1 cm) is made under sterile conditions in the skin over the thoracic region, and a pocket is prepared by blunt dissection. In certain circumstances, approximately 25 mg of the test sample is implanted deep into the pocket and the incision is closed with a metallic skin clip. The heterotropic site allows for the study of bone induction without the possible ambiguities resulting from the use of orthotopic sites.

The sequential cellular reactions occurring at the heterotropic site are complex. The multistep cascade of endochondral bone formation includes: binding of fibrin and fbronectin to implanted matrix, chemotaxis of cells, proliferation of fibroblasts, differentiation into chondroblasts, cartilage formation, vascular invasion, bone formation, remodeling, and bone marrow differentiation.

In rats, this bioassay model exhibits a controlled progression through the stages of matrix induced endochondral bone development including: (1) transient infiltration by polymorphonuclear leukocytes on day one; (2) mesenchymal cell migration and proliferation on days two and three; (3) chondrocyte appearance on days five and six; (4) cartilage matrix formation on day seven; (5) cartiliage calcification on day eight; (9) vascular invasion, appearance of osteoblasts, and formation of new bone on days nine and ten; (10) appearance of osteoblastic and bone remodeling on days twelve to eighteen; and (11) hematopoietic bone marrow differentiation in the ossicle on day twenty-one.

Histological sectioning and staining is preferred to determine the extent of osteogenesis in the implants. Staining with toluidine blue or hemotoxylin/eosin demonstrates clearly the ultimate development of endochondrial bone. Twelve day bioassays are usually sufficient to determine whether bone inducing activity is associated with the test sample.

Additionally, alkaline phosphatase activity can be used as a marker for osteogenesis. The enzyme activity can be determined spectrophotometrically after homogentization of the excised test material. The activity peaks at 9–10 days in vivo and thereafter slowly declines. Samples showing no bone development by histology should have no alkaline phosphatase activity under these assay conditions. The assay is useful for quantitation and obtaining an estimate of bone formation very quickly after the test samples are removed from the rat. For example, samples containing osteogenic protein at several levels of purity have been tested to determine the most effective dose/purity level, in order to seek a formulation which could be produced on an industrial scale. The results as measured by alkaline phosphatase activity level and histological evaluation can be represented as "bone forming units". One bone forming unit represents the amount of protein that is need for half maximal bone forming activity on day 12. Additionally, dose curves can be constructed for bone inducing activity in vivo at each step of a purification scheme by assaying various concentrations of protein. Accordingly, the skilled artisan can construct representative dose curves using only routine experimentation.

B. Bone Formation Following Implantation of Matrix-Free OP-1 Osteogenic Devices Osteogenic devices were made with 62.5 μg lyophilized OP-1, either with or without 25 mg collagen matrix. These devices were evaluated for their ability to support bone formation using the above-described rat ectopic bone formation assay, in both an intramuscular and subcutaneous site. Additionally, the mass of bone formed was assessed by measuring the calcium contents and the weights of the removed devices. The data generated is summarized in Tables 1 and 2 below.

As evidenced by both histology and calcium content, bone formed in response to all of the matrix-free OP-1 samples. These data illustrate that implanting a matrix-free OP-1 device alone is sufficient to induce endochondral bone formation in rat ectopic sites.

TABLE 1

Bone Formation vs. Concentrations of OP-1
Intramuscular Site

| Device ( ) Sample Size Collagen | OP-1 | 12 Day Implant Calcium, μg/mg tissue | Implant Weight, mg | Histology, % bone |
|---|---|---|---|---|
| 25 mg (5) | 62.5 μg | 38.2–67.1 | | 70–90 |
| 0 mg | 51.7 μg | 48.6 | 430.7 mg | 90 |
| 0 mg | 61.3 μg | 35.8 | 256.1 mg | 90 |
| 0 mg | 18.6 μg | 66.3 | 457.8 mg | 90 |
| 0 mg | 59.2 μg | 53.9 | 580.0 mg | 90 |
| 0 mg | 59.5 μg | 25.9 | 383.1 mg | 90 |

TABLE 2

Bone Formation vs. Concentrations of OP-1
Subcutaneous Site

| Device ( ) Sample Size Collagen | OP-1 | 12 Day Implant Calcium, μg/mg tissue | Implant Weight, mg | Histology, % bone |
|---|---|---|---|---|
| 25 mg (5) | 62.5 μg | 28.4–54.6 | 500.6–1472.6 | 60–80 |
| 0 mg | 40.4 μg | 44.4 | 132.7 mg | 90 |
| 0 mg | 36.7 μg | 43.9 | 337.7 mg | 80 |
| 0 mg | 35.2 μg | 37.4 | 310.7 mg | 90 |
| 0 mg | 51.0 μg | 57.5 | 195.8 mg | 90 |
| 0 mg | 51.4 μg | 29.7 | 721.9 mg | 90 |

C. Matrix-Free OP-1. Devices Containing Water-Soluble Carriers

OP-1 admixed with water soluble carriers also support bone formation. In this study, mannitol, carboxymethylcellulose, dextrin, PEG3350, a Pluronic gel and collagen each were formulated into a paste by the addition of 0.9% sterile saline. Ten $\mu$g of OP-1 dissolved in water was added to the paste to produce a matrix-free device, and the device was immediately implanted intramuscularly in rats. After 12 days, the implanted devices were removed and evaluated for bone formation by both calcium content and histology. These data confirm the above-described observation that collagen matrix is not essential for inducing volume-filling bone formation. Of the water-soluble carriers evaluated, mannitol demonstrated the best results overall, with the others appearing relatively comparable.

TABLE 3

| | Calcium, mg/mg implant | Implant $\mu$g, mg | Histology (%) |
|---|---|---|---|
| Mannitol | 100–200 | 58–48 | >90 |
| CMC | 50–200 | 28–52 | >80–90 |
| Dextrin | 20–80 | 8–12 | >90 |
| Collagen | 550–800 | 20–45 | >90 |
| PEG | 100–150 | 10–12 | >90 |
| Poloxamer | 50–150 | 14–28 | >90 |

D. Matrix-Free OP-1 Devices in Solution

Matrix-free osteogenic devices in solution also were demonstrated to induce bone formation when administered either intramuscularly (IM), or intradermally (ID). In an exemplary experiment, matrix-free OP-1 devices were prepared in 20 mM acetate buffer, pH 4.5. The devices were prepared such that the desired dose of (5–50 mg) OP-1 would be delivered in a 100 $\mu$L injection volume. Both forms of administration induced bone formation as measured by calcium content, histology and explant weight.

Poloxamer Gel-Containing Matrix-Free OP-1 Devices

Experiments currently preferred were initiated with a poloxamer formulation of the matrix-free OP-1 device. In one embodiment, this device has the unique property of being liquid at refrigeration temperatures, but gel-like when warmed to room temperature. This allows the device to be drawn up into syringe when cold, allowing for easy injection after a few minutes at room temperature. This was useful for injecting such OP-1 devices into fracture sites, since the gel permits containment of OP-1 at the site of injury.

Poloxamer gel, prepared from 0.5 g of commercially available poloxamer 407 to which 1.35 mL of water is added, is a viscous liquid at refrigeration temperature and a semisolid gel at room temperature. Bone formation was observed after 12 days in response to IM administration of matrix-free OP-1-poloxamer gel devices. The gel was not injected directly into the muscle, but was injected into the muscle flap without the use of a needle. Bone also formed in response to SC administration of these same poloxamer gel devices. The OP-1 dose (5–25 mg) was contained in 50 $\mu$l gel.

Recovery of OP-1 from the gel devices was determined by extracting with 8M urea buffer and injecting the extract onto the HPLC. 100% recovery of the OP-1 from the gel was obtained. In addition, urea extracts of selected gels were as active as an OP-1 standard. For example, one of the gels was re-extracted after 10 days storage at refrigeration temperature in a syringe; 100% recovery of OP-1 was obtained and again the extract was as active as an OP-1 standard.

As described below, sterile filtered OP-1 can be added to autoclaved or irradiated gel in an aspectic manner so that a sterile device can be provided.

OP-1 has been admixed with autoclaved poloxamer gels. The gel was prepared, autoclaved and then chilled so that it liquified prior to admixture with the OP-1. The OP-1 gel was then filled into syringes which were stored at 5° C. The samples were observed to be stable for at least 2 weeks at 50° C. Approximately at least 50–60% of the initial OP-1 remained after 7 weeks storage at 5° C. Gels were also prepared from irradiated poloxamer 407. Recoveries of 40–50% was observed after 7 weeks at 5° C.

A second time course was carried out for the purposes of evaluating bone formation in response to matrix-free OP-1-poloxamer gel devices. 50 $\mu$l volumes of poloxamer gel containing zero or 10 $\mu$g of OP-1 were injected into a muscle flap. Implants removed at day 7, 12 and 21 were analyzed for calcium content and alkaline phosphatase activity. The time course of bone formation was similar to that observed with the standard collagen-containing OP-1 device.

V. ANIMAL STUDIES: METHODS OF USE OF MATRIX-FREE OP-1 DEVICES AND IMPLANTS

A. Healing of Critical-Sized Segmental Defects in Dogs Using Matrix-Free Osteogenic Devices 1. Experiment 1

The following experiments demonstrate the efficacy of injectable and freeze-dried formulations of rhOP-1 for healing both critical and noncritical sized segmental defects in an established canine ulna defect model. Three formulations of matrix-free osteogenic devices, each containing OP-1, were evaluated in critical-size defects (2.5 cm) and/or non-critical size defects (5 mm, 3 mm, 1.5 mm). As described above, critical size defects are defects which will not heal spontaneously. The three formulations evaluated were (1) 20 mm acetate buffered solution (pH 4.5); (2) phosphate-buffered saline (PBS, approximately pH 7.5); and (3) lyophilized (freeze-dried) protein alone. The amount of OP-1 provided in the critical size defects was 1.75 mg; 0.35 mg protein was provided in the non-critical size defects. Immediately before wound closure, OP-1 was admixed with acetate or PBS and then injected at the defect site in a total of 1 ml. Lyophilized samples were placed along the length of the defect in 5 separate aliquots at discrete, non-contiguous loci along the length of the defect.

Using standard surgical techniques, osteoperiosteal segmental defects of the prescribed size were created bilaterally in the mid ulna region of twenty adult bred-for-purpose mongrel dogs. All animals were between one and two years old, weighed from 35 to 50 pounds, and were supplied by USDA licensed providers. Special attention was paid in selecting animals of uniform size and weight to limit the variability in bone geometry and loading. The animals were radiographically screened preoperatively to ensure proper size, skeletal maturity, and that no obvious osseous abnormalities existed. The animals also were screened clinically to exclude acute and chronic medical conditions during a two-week quarantine period. A complete blood count with cell differential was performed prior to surgery.

The radius was maintained for mechanical stability, but no internal or external fixation was used. The site was irrigated with saline to remove bone debris and spilled marrow cells and then dried and homeostasis was achieved prior to providing the formulation to the site. The soft-tissues were meticulously closed in layers before injection of formulations 1 or 2 (acetate or PBS). Formulation 3 devices (lyophilized protein alone) was placed along the interosseous space before closing the tissue layers to contain the implant. The procedure was then repeated on the contralateral side, except that no OP-1 device was provided before wound closure.

Animals were administered intramuscular antibiotics for four days post-surgery and routine anterior-posterior radiographs were taken immediately after surgery to insure proper placement. Animals were kept in 3×4 recovery cases for 24 to 72 hours postoperatively after which they were transferred to runs and allowed unrestricted motion.

Biweekly radiographs were taken to study the progression of healing. In addition, pre-operative blood (serum) was taken biweekly until sacrifice to study antibody formation by the sponsor. At sacrifice, all ulnae were retrieved en bloc and those that were healed sufficiently were mechanically tested in torsion. Segments were evaluated by histology for tissue response, bone architecture and remodeling, and quality and amount of new bone formation and healing.

Animals were sacrificed at 4, 6, 8 or 12 weeks post operatively.

1b(3). Radiographs

Radiographs of the forelimbs were obtained biweekly until eight weeks postoperative and then again at sacrifice at twelve postoperative weeks. Standardized exposure times and intensities were used, and sandbags were used to position the extremities in a consistent manner. Radiographs were evaluated and compared to earlier radiographs to appreciate quality and speed of defect healing.

Mechanical Testing

Immediately after sectioning, if healing was deemed sufficient by manual manipulation, specimens were tested to failure in torsion on an MTS closed-loop hydraulic test machine (Minneapolis, Minn.) operated in stroke control at a constant displacement rate of 50 mm/min in a cylindrical aluminum sleeve and cemented with methylmethacrylate using manufacturer's protocol. One end was rigidly fixed and the other was rotated counterclockwise. Since the dog ulna has a slight curvature, the specimens were mounted eccentrically to keep specimen rotation coaxial with that of the testing device. The torsional force was applied with a lever arm of six cm, by a servohydraulic materials testing system. Simultaneous recordings were made of implant displacement, as measured by the machine stroke controller, while load was recorded from the load cell. Data was recorded via an analog-to-digital conversion board and a personal computer and an online computer acquisition software. Force-angular displacement curves were generated from which the torque and angular deformation to failure were obtained, and the energy absorption to failure computed as the area under the load—displacement curve.

Results

The bone healing characteristics, mechanical strength, and histology of critical size ulna defects treated with rhOP-1 without carrier material were similar to that of defects treated with the standard OP-1 device. In brief, the experimental observations were as follows: New bone formation and healing patterns observed radiographically in defects treated with rhOP-1 without a matrix were similar to healing patterns observed previously with the conventional collagen-containing OP-1 device. In general, new bone formation was evident as early as two weeks postoperative. The new bone continued to density, consolidate and remodel until sacrifice at twelve postoperative weeks. This study demonstrated that functional bony union is possible with human OP-1 devices without matrix. Additionally, the gross appearance and the twelve week histologic characteristics were similar to that observed with the conventional collagen-containing OP-1 device. Of the six defects treated with a matrix-free OP-1 device, four had solid bony unions at twelve weeks postoperative. The remaining two defects, in the same animal, demonstrated some early new bone formation radiographically, however at sacrifice were incompletely spanned or filled with new bone. The mean torsional load to failure of the healed defects was 40.05N (This represents the equivalent of about 79% of previously tested segmental defects treated with the traditional collagen-containing OP-1 device and 61% of previously tested intact control ulna.)

Radiographically, extensive new bone formation was observed at two weeks postoperative with all three formulations. From two to 12 weeks, new bone increased in volume and radiodensity and filled and spanned the defects. By 12 weeks postoperative (sacrifice), radiodense new bone had significantly filled and bridged the defects treated with rhOP-1 formulations. All rhOP-1 defects were mechanically stable and bridged with new bone at sacrifice at 12 weeks. No significant differences were found among the three formulations for radiographic appearance, although Formulations 1 and 2 scored slightly higher than Formulation 3 at all time periods.

Histologically, proliferative new bone was present within and surrounding the defects treated with rhOP-1. Bridging of the defects and bony healing was significantly completed by 12 weeks postoperative with gaps of fibrocartilage between areas of significant new bone growth. Signs of early cortex development with densification of the new bone borders was present in all rhOP-1 defects. There were no differences in histologic grading results based upon formulation type, although Foundation 2 scored highly than Formulations 3 and 1 for quality of union.

The mean load to failure of the Formulation 1 defects was 47.64N (94% of defects treated with the standard OP-1 device and 73% of previously tested intact controls). The mean load to failure of the Formulation 2 defects was 51.96N (102% of defects treated with the standard OP-1 device and 80% of previously tested intact controls). The mean load to failure of the Formulation 3 defects was 50.86N (100% of defects treated with the standard OP-1 device and 78% of previously tested intact controls). No significant differences were noted in the mechanical testing results among formulation type. Formulation 2 defects scored slightly higher than Formulations 3 and 1 in maximum load to failure.

TABLE 4

Mechanical testing results for critical and noncritical size defects treated with rhOP-1 versus nontreated controls. Mean ± SD (sample size).

| Defect Size (Treatment) | Max Load (N) | Torque (Nm) | % of Intact Ulna |
|---|---|---|---|
| 2.5 cm (rhOP-1) | 46.11 ± 17.42(10) | 2.77 ± 1.05(10) | 70.64 ± 26.69(10) |
| 2.5 cm (control) | * | * | * |
| 5.0 mm (rhOP-1) | 51.81 ± 17.94(6) | 3.11 ± 1.08(6) | 79.37 ± 27.48(6) |
| 5.0 mm (control) | 9.20 ± 6.62(5) | 0.55 ± 0.40(5) | 14.09 ± 10.14 (5) |
| 3.0 mm (rhOP-1) | 64.10 ± 49.12(4) | 3.85 ± 2.95(4) | 98.21 ± 75.25(4) |
| 3.0 mm (control) | 21.91 ± 26.46(3) | 1.31 ± 1.59(3) | 33.57 ± 40.54(3) |
| 1.5 mm | 62.17 ± | 3.73 ± | 95.25 ± |

TABLE 4-continued

Mechanical testing results for critical and noncritical size defects treated with rhOP-1 versus nontreated controls. Mean ± SD (sample size).

| Defect Size (Treatment) | Max Load (N) | Torque (Nm) | % of Intact Ulna |
|---|---|---|---|
| (rhOP-1) | 30.48(4) | 1.83(4) | 46.70(4) |
| 1.5 mm | 19.43 ± | 1.17 ± | 29.76 ± |
| (control) | 19.11(4) | 1.15(4) | 29.28(4) |

*Defects no tested due to instability.

Formulations using 20 mm acetate buffer, pH 4.5 and 5% mannitol also were tested. Studies using non-critical size defects (5 mm gaps) showed a clear increase in the rate of healing when OP-1 was present, as compared with controls. Specifically, at 8 weeks, the controls averaged 14% the strength of intact ulnas, while the OP-1 treated defects averaged 79%. Radiographically, new bone was evident as early as two weeks postoperative and by eight weeks significantly began to fill and bridge the defects treated with rhOP-1 formulations. None of the six nontreated control defects were completely healed at the end of the study period. One of three defects with Formulation 1 (acetate buffer) and three of three defects treated with Formulation 2 (PBS) were completely filled and bridged by new bone at 8 weeks. All six defects receiving OP-1 had new bone formation and were mechanically stable. Formulation 2 defects scored significantly higher in radiographic grading results, energy absorbed to failure, and histologic quality of union that defects treated with Formulation 1. Otherwise, no differences were fund between the two formulations for mean load to failure, angular deformation and overall histologic appearance. Both formulations scored significantly higher in all categories compared to control defects. Histologically, proliferative new bone was present within and surrounding the defects treated with rhOP-1. Bridging of the defects and bony healing was almost completed by eight weeks postoperative with gaps of fibrocartilage between areas of significant new bone growth. Evidence of early cortex development and bone remodeling was present in some of the rhOP-1 defects. All nontreated controls resulted in incomplete unions although potential longer term healing was indicated by some new bone formation from the host bone ends and endosteal regions. The mean load to failure of the Formulation 2 defects was 53.23N (104.5% of critical size defects treated with the standard OP-1 device and 81.6% of previously tested intact controls). Comparison of noncritical size defects treated with 0.35 mg OP-1 to previously tested critical size defects treated with 1.5 mg OP-1 without a carrier material (Injectable Formulations) showed no significant difference in mean load to failure.

C. Healing of Fracture Defects Using Matrix-Free Osteogenic Devices

1. Rabbit Fracture Study

A rabbit fracture repair model study (ulna midshaft fracture) also demonstrates the efficacy of the methods and devices of the invention. This study compared the effect of administration of matrix-free OP-1 devices in three configurations: 1) acetate buffer pH 4.5 (soluble OP-1), 2) PBS (suspension OP-1) and 3) poloxamer gel. Four rabbits were treated in each group immediately after fracture creation; contralateral controls were no-defect arms. Animals were sacrificed 3 weeks post treatment. In summary, animals injected with the acetate- or poloxamer-containing OP-1-devices showed a significantly larger fracture callus by radiographic, gross and histological examination. The mean torsional load to failure for all ulna treated with OP-1 was 8.89±2.99 N (mean±standard deviation) (8 samples). While the mean load to failure for non-treated control ulna was 7.9±2.92 N (9 samples).

1a. Test Material Description

Matrix-free OP-1 devices in solution were utilized. The three solution configurations evaluated were: (1) rhOP-1 admixed with phosphate buffered saline, 8.71 mg OP-1/ml. The devices were packaged in individual vials. The estimated range of device volume delivered was between 30 μl and 110 μl per site; (2) rhOP-1 admixed with 20 mM acetate buffer, pH 4.5, 0.99 mg OP-1/ml. The devices were packaged in individual vials containing 130 μl. The device was drawn up into a syringe. In all cases less than 100 μl was delivered to each site. The estimated range of implant volume delivered was between 60 μl and 90 μl per site; and (3) rhOP-1 in Pluronic gel, 0.87 mg OP-1/ml. This device was packaged in a syringe. The device was kept refrigerated until administration to the defect site (lapse time less than one minute). All Thick gel was delivered in all cases using a large gauge (18) needle.

In all cases, dosages were calibrated to deliver approximately 100 μg of rhOP-1 to each fracture site.

A total of twelve adult male rabbits, adult male White New Zealand rabbits bred for purpose, at least 9 months of age at onset of study were utilized. All animals were skeletally mature and weighed between 2.4 and 3.0 kg were supplied by USDA licensed vendors. The animals were screened to exclude acute and chronic medical conditions during a quarantine period, and were radiographically screened to ensure proper size, skeletal maturity, and that no obvious osseous abnormalities exist. Specific attention was paid to selecting animals of uniform sex, size and weight to limit the variability of healed fracture strength. Experimental traverse fractures were created bilaterally in the center ulna of each animal using standard surgical techniques. The left ulna served as an untreated control in each animal. Briefly, using standard aseptic techniques, bilateral fractures were induced by making lateral incision approximately 2.0 cm in length and exposing the right ulna was obtained using sharp and blunt dissection. A transverse osteotomy was created in the mid-ulna using an electrical surgical saw. The site then was closed with resorbable suture. A matrix-free OP-1 device in solution was then injected through the soft tissues into the fracture site. The procedure was then repeated on the left side with the exception that no OP-1 device was provided to these fracture sites.

Animals were administered intramuscular antibiotics for four days post-surgery. Animals were kept in recovery cages postoperatively until fully conscious and weight bearing, after which they were transferred to standard cages and allowed unrestricted motion. The limbs were not casted.

Weekly radiographs were taken to study the progression of healing. All animals were sacrificed at three postoperative weeks. All ulna were retrieved en bloc and mechanically tested in torsion. Fracture healing was further evaluated by histology for quality and amount of new bone formation and healing.

At one week postoperative, early new bone formation was evident in all fractures. Traces of lightly radiodense material was present along the periosteal borders. The amount of new bone formation was significantly greater in fractures with OP-1 matrix-free devices than the (untreated) fractures at one week postoperative. At two weeks postoperative continuing new bone formation was evident in all fractures treated with the matrix-free OP-1 device. At three weeks, the bone callus was large and the fractures were substantially or completely healed in the presence of OP-1. On the left (non-treated) side, however, the fracture line was still evident at three weeks and the amount of callus formed was less.

The mean torsional load to failure for all ulna treated with any OP-1 device was 8.89±2.99N (8) (mean±standard deviation (sample size)). The mean load to failure for non-treated control ulnas was 7.91±2.92N (9).

Greater new bone volume and complete bridging across the fracture site was observed in all right (OP-1 device treated) fractures compared to the left. Proliferation of callus was observed that extended into the soft tissues of the treated fractures. The left (untreated) sides uniformly demonstrated new bone proliferation at the periosteal and endosteal borders and early cartilage formation at the fracture, but did not demonstrate consistent complete bony bridging of the fracture.

Consistent with the radiographic results, greater volume of new bone was observed in sites treated with OP-1 devices.

2. Goat Fracture Study

Still another animal model for evaluating enhanced fracture repair using matrix-free OP-1 devices is a goat model (tibia midshaft acute fracture). The study compares 0.5 mg of OP-1 in acetate buffer, 1 mg OP-1 in acetate buffer and 1 mg OP-1 precipitated in PBS, injected immediately after fracture creation using standard surgical techniques. Animals are followed and cared for as for the dog and rabbit studies described above and typically are sacrificed at 2, 4 and 6 weeks post treatment.

It is anticipated that enhanced fracture repair results from inclusion matrix-free osteogenic devices in these animals as demonstrated for the rabbit study.

D. Repair of Osteochondral Defects Using Matrix-Free OP-1 Devices

1. Osteochondral Defects in Rabbits

The following study demonstrates that matrix-free osteogenic devices can enhance repair of both the articular cartilage overlying the bone, as well as enhancing repair of the underlying bone. In this study, a standard rabbit osteochondral defect model was used to evaluate the various injectable forms of OP-1 to heal this kind of defect.

Matrix-free devices containing OP-1 were prepared in two different injectable delivery formulations and one freeze-dried formulation. All samples contained 125 $\mu$g OP-1. Formulation 1: 20 mM acetate buffer, pH 4.5 with 5% mannitol, 50 $\mu$l full volume; Formulation 2: Phosphate Buffered Saline (PBS) suspension; and Formulation 3: Freeze-dried in 1 sample aliquots.

A total of six adult male rabbits were utilized. Full thickness 4.0 mm in diameter osteochondral defects were created bilaterally in the patellar sulcus of each animal, for a total of 12 defects, using standard surgical techniques. The left defect received one of three OP-1 formulations and the right side defects acted as an untreated control. All animals were sacrificed at twelve postoperative weeks and the distal femurs retrieved en bloc. The defect sites were evaluated histologically and grossly as described herein above.

In all except one of the PBS group defects, the OP-1 side shows significant healing with regeneration of both the bone and cartilage. Although healing can be observed in most of the control defects without OP-1, the repair is inferior; there is usually incomplete healing of the underlying bone and a significant underproduction of glycosaminoglycans (GAG) in the cartilage (as seen by light toluidine staining).

2. Sheep Model

Osteochondral and chondral defect repair also can be evaluated in a standard goat or sheep model. For example, using standard surgical techniques, each sheep in a study is operated on both foreknee joints, and two defects per joint are created (one each on the medial and the lateral condyle). One of the joints has two standardized partial thickness chondral defects (5 mm in diameter) on each condyle, while the other joint has two similar but deeper full thickness osteochondral defects (about 1–2 mm in the subchondral bone). One joint animal is treated with a matrix-free osteogenic device formulation, and the other joint is left as an untreated control. Each group has a subgroup sacrificed early at 8 weeks and another kept for long term evaluation for 6–7 months. It is anticipated that matrix-free devices using any of the formulations described herein will substantially enhance the speed and quality of repair of both the articular cartilage and the underlying bone, consistent with the results described herein above.

E. Healing of Non-Critical Size Segmental Defects in Dogs Using Matrix-Free Osteogenic Devices 1. Experiment 2

As already exemplified in Experiment 1 above (see Section V.A.1.), injectable formulations of rhOP-1 can be used to heal non-critical size (e.g., 5 mm, 3 mm, 1.5 mm) defects. The experiment which follows is an extension of Experiment 1 and focuses on the 3 mm defect model. As is exemplified below in more detail, noncritical size (3 mm) defects treated with rhOP-1 demonstrated advanced healing and more extensive new bone formation. As demonstrated below, a 3 mm defect provided a consistent and reproducible model to evaluate acceleration of the fracture repair process.

This experiment evaluates the healing of noncritical size defects treated with two OP-1 formulations, rhOP-1 in an acetate/lactose buffer (OP/Buffer) and rhOP-1 in a carboxymethylcellulose (CMC) (OP/CMC) gel, at four weeks postoperative. The results summarized below demonstrate that noncritical size defects treated with injectable rhOP-1 in CMC solution and in an acetate buffer solution healed significantly faster compared to CMC and buffer vehicle controls and untreated controls: Radiographically, defects in both OP-1 treatment groups (OP/CMC and OP/Buffer) showed early radiodense bone formation and bridging bone by 4 weeks postoperative. The OP/CMC treated defects were almost completely filled and spanned with nonuniform density bone along the lateral ulna border and incorporating with the host bone cortices. Proliferative new bone was present in the OP/Buffer treated defects. None of the vehicle control defects (CMC and Buffer only) showed evidence of bone defect healing at 4 weeks. The histologic appearance of OP/CMC and OP/Buffer treated defects was similar. In the OP treated defects, significant amounts of new bone had formed at the defect cortices and along the ulna periosteum extending across the defect site. Bone defect bridging was nearly complete at the 4 week time period. Mineralizing cartilage and fibrous tissue were present in OP treated defects. In contrast, the vehicle control defects were filled and surrounded with fibrous tissue and had minimal amounts of new bone formation at the defect cortices. On average, the OP/CMC treated defects at 4 weeks had a torsional strength that was 51% of the strength of intact ulnas compared to 14% in the CMC vehicle controls. Defects treated with the OP/Buffer solution had a mean torsional strength that was 44% of intact ulna strength, while the buffer control defects achieved only 9% of the torsional strength of intact ulnas. Both the OP/CMC and OP/Buffer treated groups had mechanical strengths greater than untreated controls at 4 weeks (9%) and 8 weeks (27%).

Experimental Design

The test samples consisted of recombinant human osteogenic protein-1 (rhOP-1) in an injectable delivery matrix system. Two rhOP-1 formulations and two vehicle only controls were evaluated and compared to previously tested and reported nontreated control defects. Only two of these three formulations are reported here. One formulation (OP/CMC) consisted of 0.35 mg rhOP-1 in 100 μl carboxymethylcellulose (CMC) gel supplied in three sterile syringes. A second formulation (OP/Buffer) consisted of 0.35 mg rhOP-1 in 100 μl acetate buffer supplied as an OP-1 solution. The vehicle only controls consisted of 100 μl CMC gel (CMC control) supplied in three sterile syringes and 100 μl acetate buffer (Buffer control) supplied as a control solution. Samples of known amount and content were fabricated and supplied sterile by Creative BioMolecules, Inc. (Hopkinton, Mass.).

Bilateral ulna segmental defects, 3.0 mm in length, were created in all animals. The right defects received one of two rhOP-1 formulations such that three sites of each formulation were studied. The left defects received the vehicle only control containing no rhOP-1. Weekly radiographs were taken to study the progression of healing. At sacrifice, all ulnae were retrieved en bloc and if healed sufficiently, mechanically tested in torsion. Segments were evaluated by histology for tissue response, quality and amount of new bone formation and extent of healing. Adult male mongrel dogs bred for purpose were utilized in this study because of their availability, ease of handling, anatomical size, and known bone repair and remodeling characteristics. All animals were skeletally mature, weighed from 44 to 63 pounds (mean 54 lbs), and were supplied by Martin Creek Kennels, USDA number 71-B-108 (Willowford, Ak.). Special attention was paid in selecting animals of uniform size and weight to limit the variability in bone geometry and loading.

Surgery

Anesthesia was administered by intravenous injection of sodium pentothal at the dosage of 5.0 mg/lb body weight. Following induction, an endotracheal tube was placed and anesthesia was maintained by isofluorane inhalation. Both forelimbs were prepped and draped in sterile fashion. A lateral incision approximately two centimeters in length was made and exposure of the ulna was obtained using blunt and sharp dissection. The 3.0 mm sized defect was created in the mid-ulna using an oscillating saw. The radius was maintained for mechanical study and no internal or external fixation was used. The site was irrigated with saline to remove bone debris and spilled marrow cells. The soft-tissues were meticulously closed in layers around the defect. The appropriate sample formulation was then injected into the defect site as per the treatment schedule. The procedure was then repeated on the contralateral side with the appropriate sample.

Radiographs

Radiographs of the forelimbs were obtained weekly until four weeks postoperative. Standardized exposure times and intensities were used. In order to quantify the radiographic results, each radiograph was assigned a numerical score based on the grading scale described in Table 5.

TABLE 5

RADIOGRAPHIC GRADING SCALE

| | Grade: |
|---|---|
| No change from immediate postoperative appearance | 0 |
| Trace of radiodense material in defect | 1 |
| Flocculent radiodensity with flecks of new calcification | 2 |
| Defect bridge at least one point with material of non-uniform radiodensity | 3 |
| Defect bridged on both medial and lateral sides of defect with material of uniform radiodensity, cut end of the cortex remain visible | 4 |
| Same as grade 3; at least one of four cortices is obscured by new bone | 5 |
| Defect bridged by uniform new bone; cut ends of cortex are no longer distinguishable | 6 |

Sacrifice

Animals were sacrificed using an intravenous barbiturate overdose. The ulna and radius were immediately harvested en bloc and placed in saline soaked diapers. Both ulna were macrophotographed and contact radiographs taken. Soft tissues were carefully dissected away from the defect site. A watercooled saw was used to cult the ulna to a uniform length of 9 cm with the defect site centered in the middle of the test specimen.

Mechanical Testing

Immediately after sectioning, if healing was deemed sufficient by manual manipulation, specimens were tested to failure in torsion on an MTS closed-loop hydraulic test machine (Minneapolis, Minn.) operated in stroke control at a constant displacement rate of 50 mm/min. Each end of the bone segment was mounted in a cylindrical aluminum sleeve and cemented with methyl methacrylate. One end was rigidly fixed and the other was rotated counterclockwise. Since the dog ulna has a slight curvature, the specimens were mounted eccentrically to keep specimen rotation coaxial with that of the testing device. The torsional force was applied with a lever arm of 6 cm by a servohydraulic materials testing system. Simultaneous recordings were made of implant displacement, as measured by the machine stroke controller, while load was recorded from the load cell. Data was recorded via an analog-to-digital conversion voarch and a personal computer and an online computer acquisition software. Force angular displacement curves were generated from which the torque and angular deformation to failure were obtained, and the energy absorption to failure computed as the area under the load-displacement curve.

Histology

Both tested and untested specimens were prepared for histologic evaluation. The individual specimens were fixed by immersion in 10% buffered formnalin solution immediately following mechanical testing or after sectioning in untested specimens. On a water cooled diamond saw the specimens were divided by bisecting the specimen down its long axis. This procedure resulted in two portions of each specimen for different histologic preparations including undecalcified ground sections and undecalcified microtome sections.

Following fixation, t he specimens designated for undecalcified sections were hydrated in graduated ethyl alcohol solutions from 70% to 100%. The specimens were then placed in methyl methacrylate monomer and allowed to polymerize. The ground sections were obtained by cutting the specimens on a high speed, water cooled Mark V CS600-A (East Grandy, Conn.) sectioning saw into sections approximate ly 700 to 1,000 microns thick. These sections were mounted on acrylic slides and ground to 100 micron thickness using a metallurgical grinding wheel, and micro-radiographs were made using standardized techniques. Following microradiography the sections were further ground to approximately 50 microns and stained with basic fuchsin and toluidine blue for histologic grading that evaluated the quality of the union, the appearance and quality of the cortical and cancerous bone, the presence of bone marrow elements, bone remodeling, and inflammatory response (Table 6).

TABLE 6

HISTOLOGIC GRADING SCALE

| | Grade: |
|---|---|
| Quality of Union: | |
| No sign of fibrous or other union | 0 |
| fibrous union | 1 |
| osteochondral union | 2 |
| bone union | 3 |
| bone union with reorganization of cortices | 4 |
| Cortex Development: | |
| none present in the defect | 0 |
| densification of borders | 1 |
| recognizable formation | 2 |
| intact cortices but not complete | 3 |
| complete formation of normal cortices | 4 |
| Inflammatory Response: | |
| severe response | 0 |
| severe/moderate response | 1 |
| moderate response | 2 |
| mild response | 3 |
| no response | 4 |
| TOTAL POINTS: | 12 |

EXPERIMENTAL RESULTS

Radiographic Evaluation

A summary of the radiographic grades for each site is provided in Table 7. At 4 weeks postoperative, defects treated with OP/CMC had a mean radiographic grade of 3.0 out of 6 possible points. Defects treated with OP/Buffer had a mean radiographic grade of 4.0. Defects treated with CMC vehicle control and buffer only control averaged final radiographic grades of 1.33 and 1.0, respectively. In both OP-1 treated groups, OP/CMC and OP/Buffer, there were signs of radiodense new bone forming in the defects and along the lateral defect borders as early as three weeks postoperative. At four weeks, significant amounts of new bone had formed within the defects and in surrounding subcutaneous tissue. The OP/CMC defects were almost completely filled and spanned with nonuniform density bone along the lateral ulna border. New bone was significantly incorporated with the defect cortices. In two of three OP/Buffer treated defects, the host cortices remained visible although proliferative new bone was present. In contrast, none of the OP/CMC or OP/Buffer defects were completely bridged or filled by four weeks postoperative. In the CMC control group, early new bone obscured the host bone cortices at three weeks and continued to increase in radiodensity. Again, in contrast, the buffer control defects showed only a slight increase in radiodensity at the defect cortices at four weeks. None of the control defects in either group showed evidence of bony defect healing.

TABLE 7

RADIOGRAPHIC GRADING RESULTS

| Implant Type | 1 week | 2 weeks | 3 weeks | 4 weeks |
|---|---|---|---|---|
| OP/CMC | 0 | 1 | 2 | 3 |
| OP/CMC | 0 | 0 | 1 | 3 |
| OP/CMC | 0 | 1 | 2 | 3 |
| CMC Control | 0 | 0 | 1 | 1 |
| CMC Control | 0 | 1 | 1 | 2 |
| CMC Control | 0 | 0 | 0 | 1 |
| OP/Buffer | 0 | 1 | 2 | 3 |
| OP/Buffer | 0 | 1 | 2 | 4 |
| OP/Buffer | 0 | 1 | 2 | 5 |
| Buffer control | 0 | 0 | 0 | 1 |
| Buffer control | 0 | 0 | 0 | 1 |
| Buffer control | 0 | 0 | 1 | 1 |
| OP/CMC mean ± st dev (n) | 0.0 ± 0.0 (3) | 0.67 ± 0.58 (3) | 1.67 ± 0.58 (3) | 3.0 ± 0.0 (3) |
| CMC Control mean ± st dev (n) | 0.0 ± 0.0 (3) | 0.33 ± 0.58 (3) | 0.67 ± 0.58 (3) | 1.33 ± 0.58 (3) |
| OP/Buffer mean ± st dev (n) | 0.0 ± 0.0 (3) | 1.0 ± 0.0 (3) | 2.0 ± 0.0 (3) | 4.0 ± 1.0 (3) |
| Buffer control mean ± st dev (n) | 0.0 ± 0.0 (3) | 0.0 ± 0.0 (3) | 0.33 ± 0.58 (3) | 1.0 ± 0.0 (3) |

OP/CMC = 0.35 mg rhOP-1 in 100 μl CMC gel
CMC control = 100 μl CMC vehicle only gel
OP/Buffer = 0.35 mg rhOP-1 in 100 μl acetate buffer solution
Buffer control = 100 μl acetate buffer vehicle only solution

OP/CMC—4 Weeks

At one week postoperative, there were no changes in radiographic appearance of any OP/CMC defects. At 2 weeks, trace radiodense areas were present at the cut bone ends. At 3 weeks, there was an increase in radiodensity of new bone forming within the defects and along the lateral defect borders. One defect showed signs of early bony bridging. At 4 weeks, the OP/CMC defects had a significant amount of radiodense new bone both within the defect. The defects were almost completely filled and spanned with nonuniform density bone along the lateral ulna border. New bone was significantly incorporated with the defect cortices. None of the OP/CMC treated defects were completely filled or solidly bridged with new bone at 4 weeks postoperative. The final radiographic grade for each defect was 3 out of 6 possible points (mean 3.0±0.0, n=3).

CMC Control≦4 Weeks

At two weeks postoperative, there were no significant changes in radiographic appearance of any CMC control defects. At 3 weeks, the host cortices were beginning to obscure with new bone in 2 of 3 defects. At 4 weeks, the CMC defects showed some evidence of new bone activity at the defect cortices but no evidence of bony defect healing. The final radiographic grades were 1, 2 and 1 out of 6 possible points (mean 1.33±0.58, n-3).

OP/Buffer—4 Weeks

At one week postoperative, there were no changes in radiographic appearance of any OP/Buffer treated defect. At two weeks postoperative, trace radiodense areas were present within the OP/buffer defects and along the defect borders. Significant new bone formation was also seen in the subcutaneous tissues surrounding the defects. At 3 weeks, flecks of new bone appeared in the defects and new bone formed in the overlying soft tissues. At 4 weeks, there was a significant increase in radiodense new bone formation filling and bridging the OP-1 treated defects. In two of three defects the cortices remained visible although proliferative new bone filled and spanned the defects. None of the OP/Buffer treated defects were completely filled or solidly bridged with new bone at the sacrifice period of 4 weeks. The final radiographic grades were 3,4 and 5 out of 6 possible points, respectively (mean 4.0±1.0, n=3).

Buffer Control—4 weeks

At 3 weeks postoperative, there were no significant changes in radiographic appearance of any defect treated with the buffer only control. At 4 weeks, an increase in radiodensity at the cortices was observed although no signs of defect healing were evident. The final radiographic grade for each site was 1 out of 6 possible points (mean 1.0±0.0, n=3).

Gross Observations

OP-1 defects: All OP/CMC and OP/Buffer treated defects were manually stable and visibly had a mass of new bone formation at the defect site.

Vehicle control defects: None of the CMC and Buffer only control defects were manually stable at 4 weeks although all were mechanically tested.

Mechanical Testing

A summary of the mechanical testing results appears in Table 8.

OP/CMC

At 4 weeks postoperative, the mean load to failure of 3 mm defects treated with OP/CMC was 33.08±16.41N (n=3). This represented 51% of the strength of intact controls tested previously. The mean angular deformation was 31.13±15.32 degrees. The mean energy absorbed to failure was 41.64±30.52 Nm-degrees.

CMC Control

At 4 weeks postoperative, the mean load to failure of 3 mm defects treated with CMC control was 9.32±16.41N (n=3). This represented 14% of the strength of intact controls tested previously. The mean angular deformation was 33.36±25.95 degrees. The mean energy absorbed to failure was 10.53±8.62 Nm-degrees.

OP/Buffer

At 4 weeks postoperative, the mean load to failure of 3 mm defects treated with OP/Buffer was 29.03±16.79N (n=3). This represented 44% of the strength of intact controls tested previously. The mean angular deformation was 36.14±14.71 degrees. The mean energy absorbed to failure was 37.87±27.73 Nm-degrees.

Buffer Control

At 4 weeks postoperative, the mean load to failure of 3 mm defects treated with Buffer control was 5.62±1.65N (n=3). This represented 9% of the strength of intact controls tested previously. The mean angular deformation was 24.91±12.03 degrees. The mean energy absorbed to failure was 3.94±4.12 Nm-degrees.

TABLE 8

MECHANICAL TESTING RESULTS

| Implant | Maximum Load to Failure (N) | Torque (Nm) | Percent intact control (%) | Angulation | Energy absorbed to failure (Nm-degrees) |
|---|---|---|---|---|---|
| OP/CMC | 49.37 | 2.96 | 75.65 | 35.72 | 63.57 |
| OP/CMC | 16.56 | 0.99 | 25.37 | 14.04 | 6.78 |
| OP/CMC | 33.32 | 2.00 | 51.05 | 43.62 | 54.56 |
| MEAN ± STANDARD DEVIATION | 33.08± 16.41 | 1.99± 0.98 | 50.69± 25.14 | 31.13± 15.32 | 41.64± 30.52 |
| CMC Control | 12.81 | 0.77 | 19.63 | 33.26 | 14.06 |
| CMC Control | 11.00 | 8.00 | 16.85 | 59.35 | 16.83 |
| CMC Control | 4.14 | 0.25 | 6.34 | 7.46 | 0.70 |
| MEAN ± STANDARD DEVIATION | 9.32± 4.57 | 3.01± 4.33 | 14.27± 7.01 | 33.36± 25.95 | 10.53± 8.62 |
| OP/Buffer | 32.47 | 1.95 | 49.75 | 50.11 | 55.91 |

TABLE 8-continued

MECHANICAL TESTING RESULTS

| Implant | Maximum Load to Failure (N) | Torque (Nm) | Percent intact control (%) | Angulation | Energy absorbed to failure (Nm-degrees) |
|---|---|---|---|---|---|
| OP/Buffer | 43.83 | 2.63 | 67.15 | 37.53 | 51.77 |
| OP/Buffer | 10.79 | 0.65 | 16.53 | 20.78 | 5.94 |
| MEAN ± STANDARD DEVIATION | 20.03± 16.79 | 1.74± 1.01 | 44.48± 25.72 | 36.14± 14.71 | 37.87± 27.73 |
| Buffer control | 4.82 | 0.29 | 7.38 | 11.12 | 0.73 |
| Buffer control | 4.53 | 0.27 | 6.94 | 30.32 | 2.50 |
| Buffer control | 7.52 | 0.45 | 11.52 | 33.29 | 8.59 |
| MEAN ± STANDARD DEVIATION | 5.62± 1.65 | 0.34± 0.10 | 8.62± 2.53 | 24.91± 12.03 | 3.94± 4.12 |

Histology

A summary of the histologic grading results appears in Table 9. Out of 12 total points, the mean histologic grade of defects treated with OP/CMC was 7.00±0.87. The mean histologic grade of the CMC control defects was 4.50±0.87. The mean histologic grades of the OP/Buffer defects and the Buffer controls were 6.08±0.14 and 4.0±1.0, respectively.

OP/CMC

Treatment resulted in early osteochondral bridging with areas of mineralizing cartilage at four weeks. In defects treated with OP/CMC, significant new bone formation was observed in the periosteal and endosteal regions of the ulna and extended beyond the defect borders. Areas of mineralizing cartilage and some fibrous tissue were present within the defects. Bridging of the defects was not complete by four weeks. The host cortices remained visible although there were signs of new bone incorporation and remodeling.

CMC Control

No complete bony healing was observed in any CMC control defects at four weeks. Control defects resulted in fibrous unions with no signs of bony bridging. Fibrous tissue and mineralizing cartilage was observed filling and surrounding the defects. Very small amounts of new bone had formed along the ulna periosteum and at the endosteal region of the ulna near the host cortices. Signs of host cortex resorption were observed at the defect ends.

OP/Buffer

Treated defects were filled with mineralizing cartilage and fibrous tissue. New bone formed in the endosteal and periosteal regions of the ulna near the defect borders and early signs of bridging with new bone was evident although none of the defects were completely spanned. The host bone cortices showed signs of incorporation with new bone but were not completely obscured by four weeks. Some remodeling of the host bone cortices and early densification along the new bone borders was observed. New bone also formed in the subcutaneous tissue layers overlying the defect site and extended beyond the defect borders.

Buffer Control

No complete bony healing was observed in any buffer control defects at four weeks postoperative. Untreated defects exhibited fibrous unions with no signs of bony bridging; fibrous tissue was observed filling and surrounding the defects. Other untreated defects showed no sign of fibrous or other union. Very little new bone formation was observed in the buffer control defects. Endosteal new bone extended from the ulna marrow cavity and periosteal new bone formed along the lateral defect borders. The host bone ends were visible with signs of cortical resorption.

TABLE 9

HISTOLOGIC GRADING RESULTS

| Implant | Quality of Union | Cotrex Development | Inflammatory Response | Total Score |
|---|---|---|---|---|
| OP/CMC | 1.5 | 1 | 4 | 6.5 |
| OP/CMC | 3 | 1 | 4 | 8 |
| OP/CMC | 1.5 | 1 | 4 | 6.5 |
| MEAN ± STANDARD DEVIATION | 2.0 ± 0.87 | 1.0 ± 0.0 | 4.0 ± 0.0 | 7.0 ± 0.87 |
| CMC Control | 1 | 0 | 4 | 5 |
| CMC Control | 1 | 0 | 2.5 | 3.5 |
| CMC Control | 1 | 0 | 4 | 5 |
| MEAN ± STANDARD DEVIATION | 1.0 ± 0.0 | 0.0 ± 0.0 | 3.50 ± 0.87 | 4.50 ± 0.87 |
| OP/Buffer | 1.25 | 1 | 4 | 6.25 |
| OP/Buffer | 1 | 1 | 4 | 6 |
| OP/Buffer | 1 | 1 | 4 | 6 |
| MEAN ± STANDARD DEVIATION | 1.08 ± 0.14 | 1.0 ± 0.0 | 4.0 ± 0.0 | 6.08 ± 0.14 |
| Buffer control | 1 | 0 | 2 | 3 |
| Buffer control | 1 | 0 | 4 | 5 |
| Buffer control | 0 | 0 | 4 | 4 |
| MEAN ± STANDARD DEVIATION | 0.67 ± 0.58 | 0.0 ± 0.0 | 3.33 ± 1.15 | 4.0 ± 1.0 |

2. Experiment 3

Recombinant human osteogenic protein-1 (rhOP-1), when implanted in combination with bone collagen matrix, has been shown to heal critical-sized diaphyseal segmental defects in animals with the formation of new bone that is both biologically and biomechanically functional. The purpose of this study was to evaluate the efficacy of matrix-free injectable formulations of rhOP-1 for accelerating bone healing in a canine non-critical-sized defect model.

Bilateral osteoperiosteal segmental defects, 3.0 mm in length, were created in the imid-ulna of 18 adult male mongrel dogs. The radius was maintained for mechanical stability without additional fixation. Soft tissues were closed prior to injection of rhOP-l. Nine animals received rhOP-1 formulations in one defect and vehicle controls in the contralateral defect and were sacrificed at 4 weeks postoperative. Nine untreated control defects were evaluated at periods of 4, 8 and 12 weeks for comparison with the rhOP-1 treatment. Radiographs were taken at regular intervals to study the progression of healing. At sacrifice, all ulnae were mechanically tested in torsion if healing was sufficient. Undecalcified histologic sections were evaluated for quality and amount of new bone formation and extent of healing.

Radiographically, new bone formation was evident as early as two weeks postoperative in rhOP-1 treated defects and at 4 weeks, new bone bridged the defect. In contrast, vehicle control sites showed little or no bone formation at 4 weeks postoperative. Moreover, torsional strengths of defects treated with rhOP-1 were significantly greater at 4 weeks than vehicle or untreated controls at 4 weeks. Furthermore, torsional strength of treated defects at 4 weeks virtually equaled the strength of untreated controls at 12 weeks. A clear acceleration of defect healing and bone formation resulted from rhOP-1 treatment. Histologic findings correlated with radiographic and mechanical testing results.

The results of this study confirm that osteogenic proteins injected in non-critical-sized defects can accelerate defect healing, including fracture callus formation and bridging bone formation. Defects treated with rhOP-1 formed new bone significantly faster and restored fracture strength and stiffness earlier than untreated controls.

In summary, the ability of the matrix-free devices described hereinabove to substantially enhance defect repair, including accelerating the rate and enhancing the quality of newly formed bone, has implications for improving bone healing in compromised individuals such as diabetics, smokers, obese individuals, aged individuals, individuals afflicted with osteoporosis, steroidal users and others who, due to an acquired or congenital condition, have a reduced capacity to heal bone fractures, including individuals with impaired blood flow to their extremities. Such individuals experience refractory healing, resulting from a reduced capacity to promote progenitor cells, and are subject to gangrene and/or sepsis.

The methods and formulations disclosed herein provide enhanced bone repair by accelerating bone formation. Specifically, following the methods and protocols disclosed herein, the rate of bone formation, including bone callus formation and bridging can be accelerated. As exemplified herein, bridge formation occurs faster, and in a shorter time frame, allowing for more stable bone formation, thereby enhancing biomechanical strength of the newly forming bone.

It is well-known in the art that callus formation is one stage in the multi-staged healing process culminating in bone formation. Specifically, the healing process involves five stages: impact, inflammation, soft callus formation, hard callus formation, and remodeling. Impact begins with the initiation of the fracture and continues until energy has completely dissipated. The inflammation stage is characterized by hematoma formation at the fracture site, bone necrosis at the ends of the fragments, and an inflammatory infiltrate. Granulation tissue gradually replaces the hematoma, fibroblasts produce collagen, and osteoclasts begin to remove necrotic bone. The subsidence of pain and swelling marks the initiation of the third, or soft callus, stage. This stage is characterized by increased vascularity and abundant new cartilage formation. The end of the soft callus stage is associated with fibrous or cartilaginous tissue uniting the fragments. During the fourth, or hard callus, stage, the callus converts to woven bone and appears clinically healed. The final stage of the healing process involves slow remodeling from woven to lamellar bone and reconstruction of the medullary canal (see "Current Diagnosis & Treatment in Orthopedics," ed. H. B. Skinner (LANGE Medical Book Publ.)).

F. Repair of Chondral Defects with Matrix-Free Osteogenic Devices (Sheep)

1. Experiment 1

Using materials and methods similar to those described above (see relevant portions of D.2), the following study was conducted to further demonstrate that the exemplary osteogenic protein OP-1, when administered in an matrix-free device, can induce active chondrogenesis and chondral defect repair in weight-bearing joints.

As already described above, a defect is a structural disruption of the cartilage and can assume the configuration of a void, a three-dimensional defect such as, for example, a gap, cavity, hole or other substantial disruption in structural integrity. Defects in articular cartilage may extend through the entire depth of articular cartilage and or into the subchondral bone (osteochondral defects) or defects may be superficial and restricted to the cartilage tissue itself (chondral or subchondral defects).

Initially, damaged cartilage matrix undergoes degradation by metalloproteinases that are released by nearby cellular constituents. Proteolytic degradation clears damaged matrix components thereby releasing anabolic cytokines entrapped in the matrix. As currently understood, cytokines released from the matrix stimulate proliferation of chondrocytes and, importantly, synthesis of a new macromolecular matrix. The presence of clusters of proliferating chondrocytes, as determined microscopically, is one of the first indicators of a cartilage reparative response. Presumably, this repair response counters the catabolic effect of proteases and stabilizes the tissue by enhanced matrix synthesis.

Articular cartilage and repair of articular cartilage is readily studied by standard histological and histochemical means. The techniques are well-known in the art and include microscopic examination of sections of cartilage stained by any one of a number of histochemical stains including, but not limited to, toluidine blue, hematoxylin and eosin, von Kossa, safranin O, and Masson's trichrome stain. Following the application of different stains, the skilled artisan can assess the reparative response of cartilage by identification of proliferating chondrocytes and determination of the quality and quantity of matrix, such as collagen and proteoglycans, synthesized by chondrocytes.

As used herein, articular cartilage refers specifically to hyaline cartilage, an avascular, non-mineralized tissue which covers the articulating surfaces of the portions of bones in joints. Under physiological conditions, articular cartilage overlies highly vascular mineralized bone called subchondral bone. Articular cartilage is characterized by specialized cartilage forming cells, called chondrocytes, embedded in an extracellular matrix comprising fibrils of collagen (predominantly Type II collagen as well as the minor types such as Types IX and XI), various proteoglycans, including glycosaminoglycans, other proteins and water.

In this study, sheep were used as a model to assess repair of 1–2 mm total depth×7 mm total diameter chondral defects on the weight-bearing condylar surface of the knee. The defects were partial thickness chondral defects and did not involve the subchondral bone as was evident by a lack of bleeding following defect creation. Further confirmation was obtained by histology of thin sections at the time of sacrifice; the defects did not extend into subchondral bone.

The experimental protocol is provided in Table 10. Using standardized surgical techniques, a 2 mm total depth×7 mm total diameter defect was surgically made on the weight-bearing surface of each condyle of the right and left knee. The right knee served as the control knee. A liquid matrix-free OP- device (50 or 250 μg OP-1) in 20 mM sodium acetate, pH 4.5, was delivered either as a single bolus via injection into the intra-articular joint, or intermittently delivered (0.5 μL per hour for a 2 week duration; 200 μL total) via a locally implanted, subcutaneous mini-pump (ALZET® 2002, ALZA Scientific Products, Palo Alto, Calif.). Numerous suitable mini-pumps are readily available and routinely used by the skilled practitioner for delivery of pharmaceuticals and/or therapeutic agents; the skilled artisan will appreciate the preferred mode and rate of delivery under the circumstances. Healing of chondral defects was assessed by standard histological and histochemical methods.

TABLE 10

Chondral Defect Repair in Sheep

| Group | Left Knee(Matrix-free Device) | Right Knee (Cntrl) |
|---|---|---|
| I | 50 μg OP-1 | No Rx |
| II | 250 μg OP-1 | No Rx |
| III | 50 μg OP-1 via mini-pump | Vehicle via mini-pump |
| IV | 250 μg OP-1 via mini-pump | Vehicle via mini-pump |

The results collected to date of a 3 month mini-pump study (Group III and IV) reveal that matrix-free OP-1 devices can induce chondrogenesis and subsequent repair of chondral defects. Little evidence of chondral defect repair was observed at 12 weeks in the control defects. However, by standard histological and histochemical evaluation, new cartilage formation as well as fusion of the old and new cartilage was found in the matrix-free OP-1 treated animal. Using art-recognized histological and histochemical indicia as a measure of chondral repair, OP-1 stimulated the ingrowth of synovial cells into the defect area. These cells differentiated into full thickness, proteoglycan-rich articular chondrocytes and repair of the chondral defect resulted therefrom.

The healing of a partial thickness cartilage defect without subchondral bone involvement in an adult animal is unprecedented and demonstrates that active chondrogenesis is a feature of the repair process that is induced by a matrix-free osteogenic device. It is concluded from these studies that a matrix-free osteogenic device can be used to repair chondral defects in vivo. It is particularly significant that such repair can occur at a weight-bearing joint in a large animal model such as the sheep.

Other studies of chondral defect repair using matrix-free OP-1 devices ( for example, experiments as outlined in Group I and II above) are currently still in progress. Results similar to those obtained with the mini-pump delivery experimental paradigm described above are expected, that is, a single bolus of injectable matrix-free device injected into the intra-articular joint is expected to repair chondral defects in weight-bearing joints.

G. Alternative Methods of Healing Non-Critical Size Segmental Defects Using Matrix-Free Osteogenic Devices 1. Experiment 1: The Effects of Delayed Administration of Matrix-Free Osteogenic Device on Repair of Non-Critical Size Defects (Dogs)

The purpose of this study was to evaluate the healing of non-critical size defects treated with matrix-free OP-1 devices at various delayed administration times post-injury. The particular device exemplified below is an injectable formulation of the matrix-free osteogenic device. Other device embodiments are expected to yield similar results.

Briefly, the experimental observations are as follows: In general, non-critical size segmental defects treated with matrix-free OP-1 devices healed to a significantly greater degree compared to injectable carrier controls at 4 weeks post-injury. Of particular significance are the unexpected results which indicate that at least one indicia of defect healing, specifically, enhanced ulnar mechanical strength, can be enhanced by manipulating the post-injury time at which matrix-free OP-1 devices are administered.

For purposes of this experiment and as used herein, injury means accidental occurrence of a defect (such as an unexpected physical mishap resulting in the occurrence of a non-critical size defect), purposeful occurrence of a defect (such as surgical manipulation resulting in the occurrence of a non-critical size defect), or non-traumatically induced defects caused by one or more of the following diseases or disorders: hypoxia; ischemia; primary and metastatic neoplasia; infectious diseases; inflammatory diseases; so-called collagen diseases (including defects in collagen synthesis, degradation or normal matrix); congenital, genetic or developmental diseases; nutritional diseases; metabolic diseases; idiopathic diseases; and diseases associated with abnormal mineral homeostasis, to name but a few.

Certain of the methods exemplified herein contemplate the step of administering a matrix-free device to a defect site after onset of the healing process; the stages of the healing process, and the physiological events associated therewith, were earlier described. Another of the methods of the present invention comprises the step of administering a matrix-free device to a defect site during maturation of the endogenous matrix at the site; the events associated with endogenous matrix formation during endochondral bone formation were also earlier described. In a currently preferred embodiment, the present invention provides a method of repairing a bone defect, chondral defect, or osteochondral defect involving the step of administering a matrix-free device at times post-injury which are delayed. Such delays can be short-term, moderate or long-term as described below. The extent to which administration is delayed depends upon the circumstances and the skilled artisan will readily appreciate the significance thereof.

As demonstrated below, improved healing and defect repair results from administration of a matrix-free device to a defect site at elapsed times post-injury. For example, delayed administration times can include times from at least 0.5 hours to at least 6.0 hours post-injury; alternatively, delayed administration times can include times from at least 6 hours to 24 hours or from at least 24 hours to 48 hours post-injury. In one currently preferred embodiment, the delay is at least 6 hours. Other post-injury administration times are also contemplated by the instant invention. In certain other currently preferred embodiments, delayed administration times can range from at least 48 hours to at least 72 hours post-injury. In yet other embodiments, administration times can range significantly beyond 72 hours, e.g., matrix-free osteogenic devices can be administered to the defect site as late as the remodeling stage of bone healing. Also contemplated are methods wherein matrix-free osteogenic devices are administered to a non-critical size defect site at a plurality of time points post-injury. For example, a currently preferred plurality is from 0.5 to 6 hours and 7 days post-injury. A plurality of delayed administrations can be accomplished by manual delivery to the defect locus or by automated delivery using a mini-pump as described earlier.

Experimental Design

A total of 12 adult mongrel dogs were utilized. As described earlier, bilateral ulnar segmental defects, 3.0 mm in length, were created in all animals. As exemplified in this particular study, the matrix-free formulation of OP-1 used was 3.5 mg OP-1 /ml delivered in 100 $\mu$L lactose/acetate buffer as described earlier. Twelve animals were administered matrix-free devices in the right defect at various post-injury time points and control devices were administered in the left defect at various post-injury time points. Three animals were treated at defect creation (0 hours), three at 6 hours post-injury, and three at 48 hours post-injury. All animals were sacrificed 4 weeks after surgery. Weekly radiographs were taken to study the progression of healing. At sacrifice, segments of bone were evaluated by histology for tissue response, quality and amount of new bone formation, and extent of healing. All ulnae were retrieved en bloc and mechanically tested in torsion.

As described earlier, immediately after sectioning, ulna were tested to failure in torsion on an MTS closed-loop hydraulic test machine operated in stroke control at a constant displacement rate of 50 mm/min. One end was rigidly fixed and the other was rotated counterclockwise. The torsional force was applied with a lever arm of six cm, by a servohydraulic materials testing system. Simultaneous recordings were made of implant displacement, as measured by the machine stroke controller, while load was recorded from the load cell. Data was recorded via an analog-to-digital conversion board and a personal computer and on-line computer acquisition software. Force-angular displacement curves were generated from which the torque and angular deformation to failure were obtained, and the energy absorption to failure computed as the area under the load-displacement curve.

Results

All specimens were mechanically tested at 4 weeks post-surgery. Mechanically, defects receiving matrix-free OP-1 devices at 6 hours post-injury had the highest torsional strength; 73% of intact ulnae compared to 64% at 48 hours and 60% at 0 hours. The control defects at 0 hours, 6 hours, and 48 hours post-injury had strengths of 23%, 28%, and 24%, respectively.

This study demonstrates the surprising result that, in certain embodiments of the present invention, improved healing of a non-critical size defect can be achieved by delayed administration of a matrix-free osteogenic device to the defect locus post-injury. This unexpected result is related to the stage of bone healing or endogenous matrix formation at the defect site including but not limited to events such as clot formation, progenitor cell infiltration, and callus formation, particularly soft callus, to name but few. Moreover, it is expected that other defect repair processes involving bone, such as repair of osteochondral defects similar to those described herein, can be improved by delayed administration of matrix-free osteogenic devices to the defect site post-injury.

H. Further Studies of Chondral Defect Repair Using Matrix-Free Osteogenic Devices (Sheep)

1. Experiment 1: Glycosaminoglycans and Other Polymers as a Carrier for Osteogenic Protein As described earlier, certain preferred categories of compounds are suitable as carriers in the matrix-free devices contemplated herein. Among the currently preferred categories are compounds appreciated by the art as lubricating agents, especially those which occur naturally and naturally perform physiological functions such as protection and lubrication of cells and maintenance of tissue integrity, to name but a few. Such compounds are generally also wetting and moisture-preserving agents. One sub-category of currently preferred lubricating agents includes the biopolymers known as glycosaminoglycans. Glycosaminoglycans contemplated by the present invention include, but are not limited to, hyaluronic acid, chondroitin, dermatan, keratan to name but a few. Sulfonated as well as non-sulfonated forms can be used in the present invention. Other glycosaminoglycans are suitable for formulating matrix-free devices, and those skilled in the art will either know or be able to ascertain other suitable compounds using no more than routine experimentation. For a more detailed description of glycosaminoglycans, see Aspinall, *Polysaccharides*, Pergamon Press, Oxford (1970).

A particularly preferred glycosaminoglycan is hyaluronic acid (HA). HA is a naturally occurring anionic polysaccharide or complex sugar. It is found in cartilage and synovial fluid. HA is available both in cosmetic grade and medical grade; medical grade is generally preferred for use with the present invention. HA can range in molecular weight from low to high. In certain embodiments of the present invention, high molecular weight material is preferable; as an example only, HA 190 (1.9 a $10^6$Da; 1% is currently preferred, yet concentrations ranging from 0.5–2.0% are suitable) admixed with saline can be administered (0.1 ml/kg) twice weekly intra-articularly to repair chondral defects. In other embodiments, low molecular weight HA (such as HA80, $0.8\times10^6$ Da; 1% is preferred, yet concentrations less than or equal to 4% are suitable) can be used. Using the teachings provided herein, the skilled artisan can assess the circumstances under which high molecular weight HA is preferable to low molecular weight material for defect repair, and vice versa. Moreover, the skilled artisan will further appreciate that HA in solution is a viscous liquid and that the viscosity can be manipulated by adjusting the molecular weight and the HA content. For example, in some embodiments, it is preferred to approximate the viscosity of synovial fluid in the joint. Using ordinary skill and routine experimentation, together with the teachings provided herein, the skilled artisan can formulate matrix-free osteogenic devices using HA as a carrier for chondral defect repair; the viscosity of the device as well as the protein content can be readily adjusted as required by the circumstances and as taught herein. HA is available commercially from several sources including Sigma Chemical Company (St. Louis, Mo.), Genzyme Pharmaceuticals (Cambridge, Mass.) and Collaborative Laboratories (East Setauket, N.Y.).

Glycosaminoglycan and other polymeric carriers, such as hyaluronic acid, suitable for use with the instant matrix-free osteogenic devices can be evaluated in the sheep chondral defect model described above. For example, two 2×7 mm defects are made by standard surgical procedures in the weight bearing surface of the medial and lateral condyles of both knee joints in a sheep. One knee joint is treated by intra-articular administration of an OP-1/hyaluronic acid matrix-free device and the other joint is treated with hyaluronic acid alone.

Two groups of sheep are studied: Group I is sacrificed at 8 weeks and Group II is sacrificed at 6 months. As described earlier, healing of chondral defects can be assessed by radiology and standard histological and histochemical methods. Radiographs of each knee are taken at monthly intervals. Arthroscopic examination is performed using standard techniques and equipment under anesthesia just prior to sacrifice. Immediately after sacrifice, specimens of the knee joint are fixed in 10% neutral buffered formalin. Specimens are bisected longitudinally and one section decalcified in graduated ethyl alcohol solutions from 70–100%, and embedded in methylmethacrylate, sectioned and stained for histologic grading.

It is expected that hyaluronic acid-containing matrix free devices can enhance the rate of chondral defect repair and can improve the extent of repair achieved. Repair can be assessed in animal models by standard cartilage characterization methods, including histologic grading of stained and fixed tissue sections, localization of cartilage-specific macromolecules (such as type II collagen and aggrecan), determination of the proteoglycan profile and mechanical testing. All the foregoing can be accomplished by the skilled artisan using routine experimentation and the knowledge in the art.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for inducing bone formation sufficient to fill a defect locus defining a void, the device comprising:

an osteogenic protein dispersed in a biocompatible, non-rigid amorphous carrier having no defined surfaces, wherein said carrier is selected from the group consisting of poloxamers; gelatins; polyethylene glycols (PEG); dextrins; and vegetable oils; with the proviso that said osteogenic protein is not TGF-β.

2. The device of claim 1 wherein said carrier comprises a gel.

3. The device of claim 1 wherein said carrier comprises an aqueous solution.

4. The device of claim 1 wherein said carrier is selected from the group consisting of: mannitol; PEG 3350; poloxamer 407; and sesame oil.

5. The device of claim 1 wherein said osteogenic protein is selected from the group consisting of OP1; OP2, OP3, BMP2; BMP3; BMP4; BMP5; BMP6; BMP-10, BMP-11, BMP-12, BMP-15, BMP-3b, BMP9; DPP; Vg1; Vgr; 60A protein; GDF-1; GDF-3, GDF-5, GDF-6, GDF-7, GDF-8, GDF-9, GDF-10, GDF-11; and amino acid sequence variants thereof.

6. The device of claim 1 wherein said osteogenic protein is selected from the group consisting of OP1; OP2, BMP2; BMP4; BMP5; BMP6; and amino acid sequence variants thereof.

7. The device of claim 1 wherein said osteogenic protein is a morphogen, said morphogen comprising an amino acid sequence having at least 70% homology within the C-terminal 102–106 amino acids, including the conserved seven cysteine domain, of human OP-1.

8. The device of claim 1 wherein said osteogenic protein is OP1.

9. The device of claim 1 wherein said osteogenic protein is mature OP1 solubilized in a saline solution.

* * * * *